United States Patent
Okada et al.

(10) Patent No.: US 6,673,020 B2
(45) Date of Patent: Jan. 6, 2004

(54) ULTRASONIC DIAGNOSTIC APPARATUS

(75) Inventors: Takashi Okada, Mitaka (JP); Akimitsu Harada, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 0 days.

(21) Appl. No.: 09/780,201

(22) Filed: Feb. 9, 2001

(65) Prior Publication Data
US 2001/0016686 A1 Aug. 23, 2001

(30) Foreign Application Priority Data

Feb. 10, 2000 (JP) ......... 2000-032856
Apr. 25, 2000 (JP) ......... 2000-123615

(51) Int. Cl.$^7$ ................. A61B 8/12
(52) U.S. Cl. ........... 600/454; 600/428; 600/441; 600/443
(58) Field of Search ............... 600/454, 443, 600/441, 428

(56) References Cited

U.S. PATENT DOCUMENTS 4,476,874 A    10/1984   Taenzer et al.
4,630,612 A  * 12/1986   Uchida et al. ......... 600/441

(List continued on next page.)

FOREIGN PATENT DOCUMENTS

EP    0 842 638    5/1998

OTHER PUBLICATIONS

K.H. Parker and C.J.H. Jones, "Forward and backward running waves in the arteries: analysis using the method of characteristics" ASME J Biomech. Eng. vol. 112, pp. 322–326, 1990.

C.J.H. Jones, M. Sugawara, R.H. Davies, Y. Kondoh, K. Uchida, and K.H. Parker, "Arterial wave intensity: physical menaing and physiological significance". In: S. Hosoda, T. Yaginuma, M. Sugawara, M.G. Taylor, and C.G. Caro (eds), Recent progress in cardiovascular mechanics, Hardwood Academic Publishers, Chur, Switzerland, pp. 129–148, 1994.

M.Sugawara, "Wave Intensity analysis: a new method for the dynamic study of heart–vessle interactions", Proceedings of the European Medical & Biological Engineering Conference, vol. 37, Suppl. 2, pp. 24–27, 1999.

M. Sugawara, K. Niki, H. Furuhata, S. Ohnishi, and S. Suzuki, "Relationship between the pressure and diameter of the carotid artery in humans" Heart Vessels, vol. 15, pp. 49–51, 2000.

A. Harada, T. Okada, M. Sugawara, and K. Niki, "Development of a non–invasive real–time measurement system of wave intensity", to be published in the 2000 IEEE Ultrasonics Symposium Proceedings.

* cited by examiner

Primary Examiner—Marvin M. Lateef
Assistant Examiner—William C. Jung
(74) Attorney, Agent, or Firm—Koda & Androlia

(57) ABSTRACT

To accurately measure wave intensity as an evaluation value using an ultrasonic diagnostic apparatus, a measurement line is set in a tomogram and anterior and posterior walls of a blood vessel are tracked on the measurement line, so that a change waveform concerning a blood vessel diameter is prepared. A tracking gate S is set on the measurement line, so that a blood velocity change waveform is prepared based on echo data concerning a part within the tracking gate S, the change waveform indicating averaged blood velocity. Wave intensity is calculated based on the blood vessel diameter change waveform and the blood velocity change waveform. Prior to the calculation of wave intensity, the blood vessel diameter change waveform is calibrated based on the maximum and minimum blood pressure values into a blood pressure waveform. A beam for Doppler measurement may be set intersecting with the displacement measurement beam.

33 Claims, 17 Drawing Sheets

U.S. PATENT DOCUMENTS

| | | | |
|---|---|---|---|
| 4,830,016 A | * | 5/1989 | Tamano et al. ............. 600/441 |
| 5,038,788 A | * | 8/1991 | Satake ........................ 600/455 |
| 5,107,840 A | | 4/1992 | Bonnefous |
| 5,280,787 A | * | 1/1994 | Wilson et al. .............. 600/441 |
| 5,450,850 A | | 9/1995 | Iinuma |
| 5,462,058 A | * | 10/1995 | Yamada et al. ............. 600/454 |
| 5,551,434 A | * | 9/1996 | Iinuma ....................... 600/455 |
| 5,573,012 A | * | 11/1996 | McEwan .................... 600/428 |
| 5,682,896 A | | 11/1997 | Scheib et al. |
| 5,724,974 A | * | 3/1998 | Goodsell et al. ............. 600/453 |
| 5,760,024 A | * | 6/1998 | Macnamee ................. 514/165 |
| 5,785,655 A | * | 7/1998 | Goodsell et al. ............. 600/441 |
| 5,997,480 A | * | 12/1999 | Sumanaweera et al. ...... 600/454 |
| 6,126,603 A | * | 10/2000 | Hatfield et al. ............. 600/443 |
| 6,222,948 B1 | * | 4/2001 | Hossack et al. ............. 348/443 |
| 6,261,233 B1 | * | 7/2001 | Kantorovich ............... 600/454 |

* cited by examiner

ULTRASONIC DIAGNOSTIC APPARATUS

BACKGROUND OF THE INVENTION

1. Field of the Invention

The present invention relates to an ultrasonic diagnostic apparatus, and in particular to an apparatus for measuring blood vessel diameter, blood flow velocity, or the like.

2. Description of the Related Art

Ultrasonic diagnostic apparatuses are used for diagnosing blood vessel condition, heart functionality, and the like. When measuring displacement of a blood vessel wall using an ultrasonic diagnostic apparatus, the blood vessel wall is automatically tracked on the path of an ultrasonic beam passing across the blood vessel based on the echo data. Displacement as time passes of a blood vessel wall is in synchronism with a heart beat. Observation of the heart beat in this manner can provide fundamental data for use in diagnosing diseases, such as heart failure, arterial sclerosis, and so on.

For measurement of the speed of a bloodstream within a blood vessel using an ultrasonic diagnostic apparatus, a sample gate is securely provided on the path of an ultrasonic beam within a blood vessel, and Doppler information can be extracted from echo data concerning the inside of the sample data. Based on the extracted Doppler information, a blood velocity (an averaged-speed within the sample gate) is calculated. The resultant data on a blood velocity is fundamental data useful in diagnosing the condition of the heart and blood vessels.

Conventional ultrasonic diagnostic apparatuses measure displacement of a blood vessel wall and a blood velocity in different measurement modes.

Meanwhile, a new evaluation value, wave intensity, has been established as a diagnostic index. Originally, wave intensity was proposed as an index for determining which of the functions of forward pulse waves and backward pulse waves is dominant, the forward pulse wave being a pulse wave traveling from the heart to periphery, the backward pulse wave being a pulse wave returning from periphery to the heart. Specifically, wave intensity is defined as follows.

$$I = \Delta P \cdot \Delta U \quad (1)$$

wherein P is blood pressure at a local part within an artery, U is blood velocity at the local part, and ΔP and ΔU are respective changes in P and U during a period Δt.

That is, wave intensity is defined as the product of changes in pressure P and blood velocity U during a constant short time period Δt. The magnitude of "I" depends on as the definition of Δt. Meanwhile, time-normalized wave intensity, which has the same property as that of the above "I" and is normalized with respect to time, can be expressed as follows.

$$WI = (dP/dt) \cdot (dU/dt) \quad (2)$$

In the equation (2), wave intensity WI is defined as the product of time differential of blood pressure P and that of blood velocity U.

One method proposed for measuring wave intensity includes a noninvasive measurement method using ultrasonic. In this method, an ultrasonic echo tracking method and an ultrasonic Doppler method are combined.

Specifically, in order to measure, for example, wave intensity in the carotid artery of a subject, conventionally, an ultrasonic probe which comprises one transducer (first transmitter/receiver) for blood vessel wall measurement and one transmission transducer and two beam receiver transducer for Doppler measurement (second transmitter/receiver) is abutted on the cervical part of the subject. Then, ultrasonic pulses are transmitted to receive echo using the first transmitter/receiver, so that the wall position of the carotid artery is automatically tracked based on the echo data. Based on the tracking, a change of a blood vessel diameter is measured. Meanwhile, ultrasonic pulses are successively transmitted to receive echoes using the second transmitter/receiver, and Doppler information is extracted from the echo data to be analyzed. Based on the analysis, a change as time passes of blood velocity is measured.

A close correlation between a change of a blood vessel diameter and that of blood pressure has conventionally been understood. Therefore, a change waveform concerning a blood vessel diameter can be regarded as a change waveform concerning blood pressure by considering the largest and smallest blood vessel diameters respectively as the maximum and minimum blood pressure values, which are measured using a cuff-type hemodynamoneter applied to the upper arm of the subject.

Further, wave intensity can be obtained in an off-line calculation using the above equation (2) based on a change of blood velocity and that of blood pressure.

In the above conventional method, however, the tomogram of a blood vessel cannot be displayed as the first transmitter/receiver comprises a single transducer for an A mode. This makes it impossible to visually confirm that an ultrasonic beam is passing across the center of a blood vessel, which in turn can lead to problems with the reliability of measurement. Moreover, while a sample point for Doppler information, which is a point where the transmission beam and two reception beams formed by the second transmitter/receiver intersect with one another, is fixedly positioned, it is uncertain whether or not the sample point falls on the center of a blood vessel. When a sample point be set close to, or on, an interior wall of a blood vessel, or even in the outside of a blood vessel, measurement accuracy is significantly deteriorated. That is, measurement reliability can not be guaranteed.

In a general view, no conventional ultrasonic diagnostic apparatus can simultaneously display a tomogram, a waveform concerning displacement of a blood vessel wall (or a blood vessel diameter), and a blood velocity waveform. In addition, no conventional ultrasonic diagnostic apparatus has a function for automatic real-time measurement of wave intensity.

Here, in order to measure displacement of a blood vessel wall and a blood velocity, the direction of an ultrasonic beam relative to the blood vessel wall or a bloodstream must be known. However, conventionally, there is a problem that it is difficult to set an ultrasonic beam intersecting with a blood vessel wall or a bloodstream at a predetermined angle. Moreover, there is another problem in simultaneous measurement of displacement of a blood vessel wall and a blood velocity, that it is difficult to set separate beam directions preferable to the respective measurements.

SUMMARY OF THE INVENTION

The present invention has been conceived in light of the above situation, and with an object of improvement of reliability in ultrasonic measurement of a tissue such as a blood vessel.

Another object of the present invention is achievement of highly accurate simultaneous measurement of blood velocity and change of a blood vessel diameter.

Still another object of the present invention is simultaneous, real-time display of a plurality of measured information concerning a blood vessels and on the like, so that comprehensive diagnosis of such can be achieved.

In order to achieve the above objects, an ultrasonic diagnostic apparatus according to the present invention transmits an ultrasonic pulse and obtains echo data in respective measurements of displacement of a blood vessel wall and of a blood velocity. Then, a tomogram of a blood vessel is prepared based on the echo data, and a measurement line relative to the blood vessel axis is automatically or manually set in the tomogram. When the position of a blood vessel wall on the measurement line is specified, the specified position is tracked so as to calculate displacement of the blood vessel wall. In addition, using the measurement line as a reference, a sample gate is set within the blood vessel, for use in extraction of Doppler information. Using the Doppler information extracted from echo data, the speed of a bloodstream flowing in the sample gate is calculated. Then, an evaluation value is calculated based on the displacement of the blood vessel wall and the blood velocity.

With the above arrangement, an ultrasonic pulse is transmitted in the respective measurements of displacement of a blood vessel wall and of a blood velocity. That is, according to a pulse Doppler method, a range resolution can be obtained, and a sample gate can be freely set within a blood vessel for extraction of Doppler information. Generally, transmission of a broadband ultrasonic pulse for measuring displacement of a blood vessel wall and that of a narrow band ultrasonic pulse for measuring blood velocity are separately executed in a time sharing manner in various possibly set pulse transmission patterns.

Various evaluation values can be calculated, with the most preferable of these being the wave intensity which is described by the above equations (1) or (2). The evaluation values may be used as parameters for other calculations.

According to another aspect of the present invention, the ultrasonic diagnosis apparatus calculates a blood vessel diameter based on the position of the blood vessel wall specified on the measurement line. Using as a reference the input maximum and minimum blood pressure values, a change of the blood vessel diameter is converted into a change of blood pressure. Then, using the thus calculated blood pressure and the blood velocity at the sample gate, calculated using the Doppler information contained in the echo data, an evaluation value is calculated.

In this arrangement, the diameter of a blood vessel is converted into blood pressure (pressure at a focused part in a blood vessel) according to the maximum and minimum blood pressure values (or a blood pressure signal) input. That is, blood pressure is estimated from the diameter of a blood vessel utilizing conventionally known knowledge concerning strong relationship between a change of the diameter of a blood vessel and a change of blood pressure.

Desirably, the evaluation value calculator for calculation of an evaluation value may include means for calculating a time differential of the blood pressure, means for calculating a time differential of the blood velocity, and means for calculating wave intensity based on the time differentials of the blood pressure and of the blood velocity.

According to still another aspect of the present invention, a time differential of the speed of a bloodstream flowing in a measurement part within a blood vessel, which is obtained based on the echo data, is obtained. Further, a time differential of the blood pressure at the measurement part, which is obtained based on the echo data and/or a bio-signal, is also obtained. Then, the time differentials of the blood velocity and of the blood pressure at the same moment are multiplied by each other to thereby calculate wave intensity.

According to yet another aspect of the present invention, the ultrasonic diagnostic apparatus sets a beam direction passing across a blood vessel, and transmits an ultrasonic pulse in the beam direction to obtain echo data in that beam direction. Based on the echo data concerning that beam direction, the positions of the anterior and posterior walls of the blood vessel are specified, and a blood vessel diameter is calculated based on the specified positions of the anterior and posterior walls of the blood vessel.

Change of the blood vessel diameter over time is converted into change of blood pressure value over time, and the pressure is used in at least one of image formation and data calculation.

This arrangement makes it possible to obtain blood pressure information which can not be obtained using a conventional ultrasonic diagnosis apparatus. Therefore, various operations or imaging using a blood pressure value are achievable. For example, the magnitude of blood pressure may be indicated by means of color-coding the blood vessel tomogram.

According to yet another aspect of the present invention, the ultrasonic diagnosis apparatus prepares a blood velocity graph showing change over time of the velocity of blood flowing in a blood vessel based on echo data, and a blood vessel diameter graph showing a change over time of a blood vessel diameter based on the echo data. The apparatus then calculates an evaluation value from the blood velocity and the blood vessel diameter obtained at the same moment, and prepares an evaluation value graph showing a change as time passes of the evaluation value. The blood velocity graph, the blood vessel diameter graph, and the evaluation value graph are simultaneously displayed.

According to yet another aspect of the present invention, the ultrasonic diagnostic apparatus prepares a tomogram of a blood vessel based on echo data. The apparatus also prepares a blood velocity graph showing change over time of the velocity of blood flowing in the blood vessel based on the echo data, and a blood vessel diameter graph showing change over time of a blood vessel diameter based on the echo data. The tomogram of the blood vessel, the blood velocity graph, and the blood vessel diameter graph are simultaneously displayed.

According to yet another aspect of the present invention, the ultrasonic diagnostic apparatus transmits and receives an ultrasonic pulse for ultrasonic beam scanning to obtain a received signal. Based on the received signal, a first beam direction is determined so as to be orthogonal to the blood vessel wall, and set to the transmitter-receiver. Then, displacement of a blood vessel wall is measured using the received signal corresponding to the first beam direction, and an evaluation value is calculated using the displacement of the blood vessel wall. This arrangement allows the transmitter-receiver to control the direction of an ultrasonic beam (a position of a beam axial line) transmitted and received by a probe. As a result, the first beam direction can be automatically set so as to be orthogonal to the blood vessel wall based on the received signal.

DESCRIPTION OF THE PREFERRED EMBODIMENTS

Figure 1:
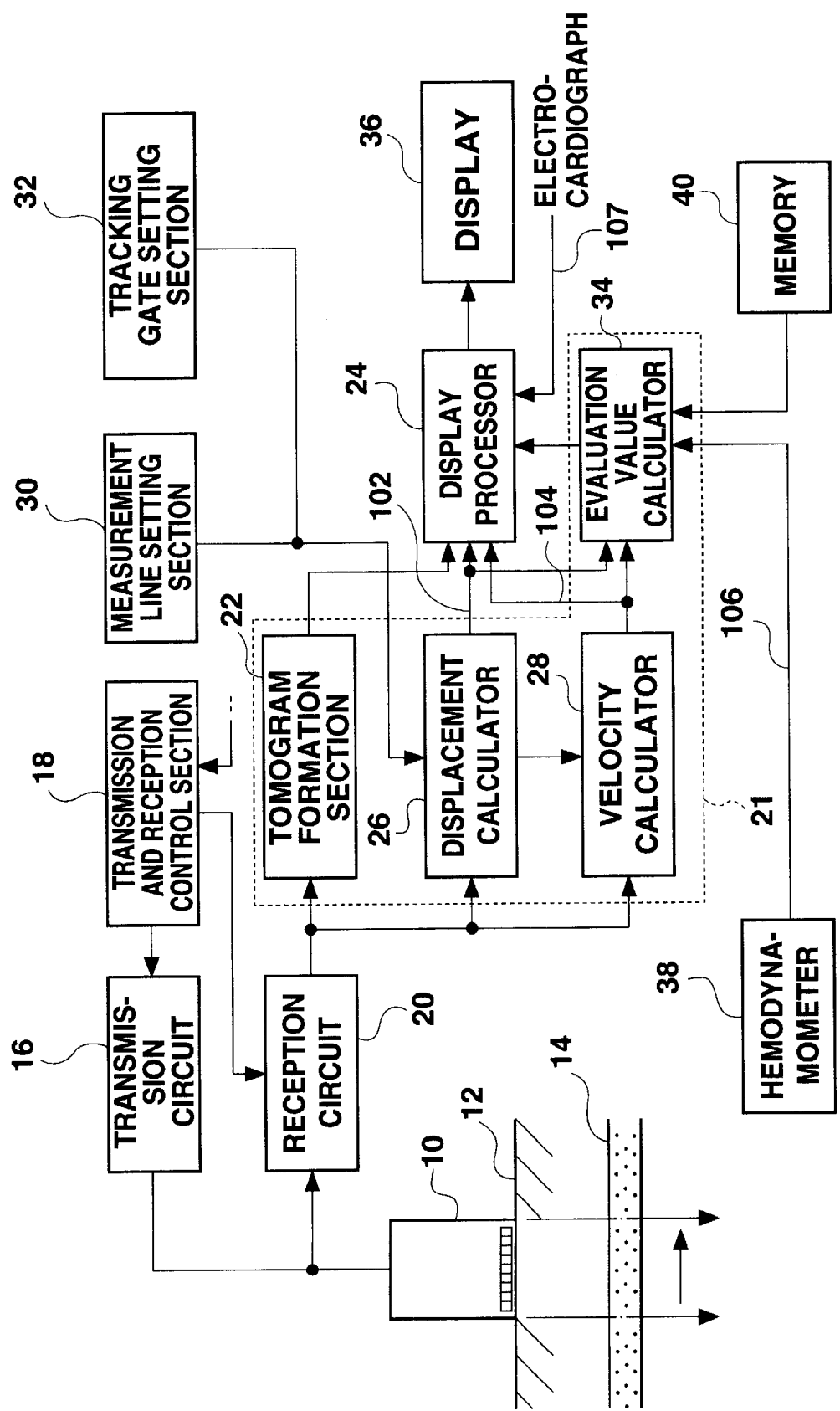
FIG. 1 is a block diagram showing a complete structure of an ultrasonic diagnostic apparatus as a first preferred embodiment of the present invention.

In the following, preferred embodiments of the present invention will be described based on the accompanying drawings.

Embodiment 1

An ultrasonic diagnostic apparatus according to a first preferred embodiment of the present invention may comprise transmitter-receiver for transmitting an ultrasonic pulse and obtaining echo data; a tomogram generator for forming a tomogram of a blood vessel based on the echo data; a measurement line setting device for setting a measurement line in the tomogram; a displacement calculator for calculating displacement of a blood vessel wall on the measurement line; a sample gate generator for setting a sample gate using the measurement line as a reference; a blood velocity calculator for calculating blood velocity at the sample gate; and an evaluation value calculator for calculating an evaluation value based on the displacement of the blood vessel wall and the blood velocity.

In this structure, an ultrasonic pulse is transmitted in the respective measurements of blood vessel wall displacement and of blood velocity. That is, according to a pulse Doppler method, a range resolution can be obtained, and a sample gate can be freely set within a blood vessel for extraction of Doppler information. Generally, transmission of a broadband ultrasonic pulse for measuring displacement of a blood vessel wall and that of a narrowband ultrasonic pulse for measuring blood velocity are separately conducted in a time sharing manner in various possibly set pulse transmission patterns.

With the above structure, desirably, ultrasonic beam 2D scanning is conducted by means of either a mechanical or electronic manner so that a data acquisition area (a scanning plane) is formed. Desirably, the position where and the posture in which an ultrasonic probe abuts a subject body are adjusted such that the scanning plane is formed so as to include the center axis of a blood vessel. The adjustment can be readily achieved through observation of a displayed tomogram. The 3D scanning may be carried out using an ultrasonic beam.

When a tomogram is set including the center axis of a blood vessel, a measurement line is automatically or manually set relative to the blood vessel axis in the tomogram. Then, the inner or outer surface of the blood vessel wall on the measurement line is specified. Desirably, the inner surface of the wall closer to the ultrasonic probe (i.e., the wall on this side when viewed from the ultrasonic probe side, or an anterior wall) and that of a farther wall (i.e., the wall on other side, or a posterior wall) are specified. Then, the diameter of the blood vessel is calculated based on the distance between the inner walls. In this case, a known echo tracking method may be used.

For rational search for a blood vessel wall, desirably, an automatic search area may be set prior to the search. For a measurement line not orthogonal to the blood vessel axis, angle correction may be given to the resultant data according to the intersecting angle between the line and the axis. Generally, a measurement line is set in one of the directions of an ultrasonic beam, though it may be set in any direction in the tomogram. In either case, desirably, a measurement line is set so as to be orthogonal to a blood vessel axis.

Desirably, a sample gate is adaptively set at the center of a blood vessel on a measurement line. The sample gate may have a width adapted to variable setting, or may be set as a substantial point. A sample gate may be set either automatically or manually. It is preferable, when the position of a blood vessel wall has already been specified, that a sample gate be dynamically set so as to follow the specified position of the blood vessel wall. For example, desirably, a sample gate is automatically set such that its center coincides with the middle between the anterior and posterior wall positions.

The above described automatic sample gate setting and blood vessel wall tracking enable highly accurate measurement while following displacement, if any, of an entire blood vessel or a change in the posture of an ultrasonic probe due to the subject's breathing. It is desirable in the above structure that the depth and width of a sample gate be variably set so that a sample gate can be set in an appropriate position relative to a blood vessel according to the subject's body construction and so on. This arrangement enables highly accurate measurement.

Using Doppler information contained in echo data concerning the inside of a sample gate, blood velocity (generally, an averaged speed of a bloodstream flowing within a sample gate) is calculated. For the calculation, for example, a known auto-correlation method may be applicable, as well as an FFT processing. When a measurement line is set orthogonal to a blood vessel axis, it is difficult, in view of the Doppler measurement principle, to measure blood velocity through ultrasonic transmission and reception in that direction. In such cases, therefore, it is desirable that a Doppler measurement direction be separately set so as to intersect with the measurement line at the center of the blood vessel so that an ultrasonic beam for Doppler measurement is additionally transmitted in that direction.

It should be noted that, when a plurality of reception beams are set for one transmission beam in directions different from that of the transmission beam, a blood velocity vector can be obtained and various corrections (e.g., blood velocity correction) can be made using such a blood velocity vector.

From the accurate measurements of displacement of a blood vessel wall (or a change of a blood vessel diameter) and blood velocity obtained as described above, a predetermined evaluation value is obtained. Various evaluation values are possible, with the most preferable of these being the above-described wave intensity. The evaluation values may be used as a parameter for other calculations.

In an ultrasonic diagnosis apparatus of the present invention, desirably, a displacement waveform indicative of displacement a blood vessel wall over time and a velocity waveform indicative of a change over time of blood velocity may be displayed together with a tomogram.

This arrangement enables confirmation of the relationship between the blood vessel and the applied ultrasonic beam through observation of the tomogram. Therefore, the position where and the posture in which the ultrasonic probe abuts on the subject can be desirably adjusted, enabling accurate manual setting of a measurement line. Moreover, simultaneous displaying of a displacement waveform and a velocity waveform enables comprehensive diagnosis of the cardiovascular system, such as a blood vessel, with reference to the mutual correlation between the waveforms.

Desirably, an evaluation value waveform indicative of a change over time of an evaluation value may additionally be shown. This arrangement enables analysis of the tendency of a time-dependent change of an evaluation value based on the evaluation value waveform. In addition, the simultaneous displaying of a displacement waveform and a velocity waveform enables consideration of the background underlying the resultant evaluation value.

Desirably, a bio-signal waveform may additionally be shown. A bio-signal waveform is a waveform indicative of electrocardiogram, phonocardiogram, and so on. Additional consideration of such auxiliary information enables further accurate diagnosis of a blood vessel and so on.

Desirably, the displacement waveform, the velocity waveform, the evaluation value waveform, and the bio-signal waveform are shown on a real time basis with their time axes aligned in parallel. That is, advantageously, data measurement and data calculation can be performed simultaneously.

Desirably, the measurement line setting device is a means for designating a measurement line by a user, and may include a pointing device such as a keyboard, a track ball, and so on.

Desirably, an apparatus of the present invention may further comprise means for tracking a position of a blood vessel wall on the measurement line while following any motion of the blood vessel wall, so that the apparatus calculates any such displacement of the blood vessel wall based on the result of position tracking of the blood vessel wall. Desirably, discrimination using a threshold and specific phase following detection is conducted for blood vessel wall tracking. For this purpose, known methods are applicable. The positions of the anterior and posterior walls are specified so that the diameter of the blood vessel can be promptly calculated based on the distance between the walls.

Desirably, the sample gate generator dynamically sets a sample gate within the blood vessel so as to follow the position of the blood vessel wall tracked. Specifically, a sample gate can be set using, as a reference, a predetermined distance from the anterior wall toward the inside of the blood vessel or the middle between the anterior and posterior walls of the blood vessel. Alternatively, blood velocities may be measured at a plurality of points in a direction orthogonal to the blood vessel axis within the blood vessel and the point showing the highest velocity may be used as a reference in sample gate setting.

Desirably, the direction of the measurement line may be determined as a first beam direction for displacement measurement, and a direction passing through the sample gate and intersecting with the measurement line is determined as a second beam direction for Doppler measurement. This arrangement enables acquisition of data for use in evaluation value calculation, under angular condition appropriate for both displacement measurement and Doppler measurement (blood velocity measurement). It is obvious that one ultrasonic beam may be used for both displacement and Doppler measurements.

Desirably, the transmitter-receiver includes an array transducer comprising a plurality of ultrasonic transducer elements, and the array transducer carries out transmission and reception of an ultrasonic beam in the first direction and that in the second direction in a time sharing manner. In such a case, first and second beams are desirably transmitted and received via parts on the array transducer. Desirably, the direction of a second beam is dynamically corrected following a change, if occurs, of the position of a sample gate. Note that transmission and reception beams can be formed, as known, through delay control of signals to be supplied to the various transducer elements and phasing integration to signals received therefrom.

An ultrasonic diagnostic apparatus according to the present invention may comprise a blood vessel diameter calculator for calculating a blood vessel diameter along the measurement line; a Doppler calculator for calculating blood velocity at a sample gate, which was set using the measurement line as a reference; a blood pressure calculator for converting a change of the blood vessel diameter to a change of blood pressure using a maximum blood pressure value input and a minimum blood pressure value input, as a reference; and an evaluation value calculator for calculating an evaluation value based on the blood pressure and the blood velocity.

With this arrangement, a blood vessel diameter is converted into a blood pressure value (pressure at a focused part in a blood vessel) according to the maximum and minimum blood pressure values (or a blood pressure signal) input. That is, blood pressure is estimated from a blood vessel diameter utilizing the conventionally known knowledge concerning strong relationship between a change of a blood vessel diameter and a change of blood pressure.

Desirably, for the conversion into blood pressure, the blood pressure calculator considers the largest blood vessel diameter as the maximum blood pressure value and the smallest blood vessel diameter as the minimum blood pressure value. Also desirably, the maximum blood pressure value and the minimum blood pressure value are measured using a hemodynamometer applied to a specific part of a subject. The maximum and minimum blood pressure values may be manually input or may be read from stored data. Further, a catheter type blood pressure sensor may be inserted into a concerned blood vessel or a concerned part so that a conversion coefficient may be obtained based on an output of the sensor and an actually measured value of blood pressure on the arm.

An apparatus of the present invention may further comprise means for calculating a time differential of the blood pressure, means for calculating a time differential of the blood velocity, and means for calculating wave intensity based on the time differentials of the blood pressure and the time differential of the blood velocity. Time differential calculation may be conducted by simply obtaining a data difference caused in a predetermined very short period.

A blood pressure value may be obtained using echo data and/or a bio-signal. A coefficient may be multiplied to the echo data when only the echo data is used. Alternatively, a change of a blood vessel diameter, obtained based on echo data, may be calibrated using a blood pressure value either externally supplied or accurately measured using a catheter type blood pressure sensor.

Desirably, an apparatus of the present invention may further comprise means for forming and displaying on a display screen a tomogram of a blood vessel based on the echo data; and means for displaying a mark standing for a measurement part in the tomogram of a blood vessel displayed on the display screen. The displayed mark enables confirmation of a measurement part in the tomogram, which can resultantly improve measurement reliability.

Desirably, an apparatus of the present invention may further comprise means for displaying a waveform indicative of a change as time passes of the wave intensity, together with the tomogram of the blood vessel.

Also, an apparatus of the present invention may further comprise means for setting a beam direction passing across a blood vessel, transmitting an ultrasonic pulse in the beam direction, and obtaining echo data in the beam direction; means for specifying the positions of an anterior wall and a posterior wall of the blood vessel based on the echo data obtained in the beam direction; means for calculating a blood vessel diameter based on the positions of the anterior wall and the posterior wall of the blood vessel; and means for converting a change as time passes of the blood vessel diameter to a change as time passes of a blood pressure value. In the apparatus, the blood pressure value is used in at least one of image formation and data calculation.

Such an arrangement makes it possible to obtain blood pressure information which could not have been obtained using a conventional ultrasonic diagnosis apparatus. Therefore, various operations or imaging using a blood pressure value are achievable. For example, the magnitude of blood pressure may be indicated by means of coloring on the tomogram of a blood vessel.

Desirably, change over time of a blood vessel diameter is converted into a change over time of a blood pressure value according to reference data. Desirably, the reference data is obtained using a hemodynamometer externally applied to a specific part of a subject.

An ultrasonic diagnostic apparatus of the present invention may comprise means for preparing a blood velocity graph showing change over time of velocity of blood flowing in a blood vessel based on echo data; means for preparing a blood vessel diameter graph showing change over time of a blood vessel diameter based on the echo data; means for calculating an evaluation value from the blood velocity and the blood vessel diameter at a same moment and preparing an evaluation value graph showing a change as time passes of the evaluation value; and means for simultaneously displaying the blood velocity graph, the blood vessel diameter graph, and the evaluation value graph.

An ultrasonic diagnostic apparatus of the present invention may comprise means for forming a tomogram of a blood vessel based on echo data; means for preparing a blood velocity graph showing change over time of the velocity of blood flowing in the blood vessel based on the echo data; means for preparing a blood vessel diameter graph showing a change as time passes of a blood vessel diameter based on the echo data; and means for simultaneously displaying the tomogram of the blood vessel, the blood velocity graph, and the blood vessel diameter graph.

In the following, a specific example of an apparatus of the present invention will be described.

FIG. 1 is a block diagram showing a complete structure of an example apparatus according to the first preferred embodiment of the present invention. The ultrasonic diagnosis apparatus has a function for calculating the above described wave intensity as an evaluation value for use in evaluation of heart functions and blood vessel condition.

Referring to FIG. 1, a probe 10 is an ultrasonic probe for transmission of an ultrasonic pulse and reception of an echo. The probe 10 has an array transducer (described later) so that ultrasonic electronic scanning is carried out through control of driving timing of the array transducer. An electronic scanning method may include, for example, electronic linear scanning, electronic sector scanning, and so on. The ultrasonic diagnostic apparatus in this example has a function for measuring wave intensity as described above. In wave intensity measurement, a position where or a posture in which the probe 10 abuts on a subject surface 12 is manually adjusted such that a data acquisition area (a scanning plane) is formed through ultrasonic scanning, so as to include the center axis of a blood vessel 14.

A transmission circuit 16 is a circuit for supplying a transmission signal to the probe 10, of which operation is controlled by a transmission and reception control section 18. A reception circuit 20 is a circuit for conducting amplification and phase integration with respect to a signal received from the probe 10, of which operation is also controlled by the transmission and reception control section 18.

The transmission and reception control section 18 is responsible for transmission and reception control for formation of a transmission beam and a reception beam. The transmission and reception control section 18 has a function, as will be described below, for setting a Doppler beam direction according to the position of a sample gate set on the scanning plane. When the sample gate is displaced, the transmission and reception control section 18 dynamically changes a Doppler direction and a sample depth according to the displacement, which will be described below.

A received signal processor 21 comprises a tomogram formation section 22, a displacement calculator 26, a velocity calculator 28, and an evaluation value calculator 34.

The tomogram formation section 22 forms a tomogram, or a B mode image. Image information concerning the formed tomogram is output to the display processor 24. The displacement calculator 26 calculates displacement of the position of a blood vessel wall, specifically, the positions of an anterior wall of a blood vessel, or a wall located on this side when viewed from the probe 10 side, and a posterior wall, or a wall located other side. The displacement calculator 26 has a function for calculating a blood vessel diameter based on the positions of the anterior and posterior walls.

Specifically, the displacement calculator 26 has a function for tracking the position of a blood vessel wall on a measurement line (described later) using a tracking gate set by a user. The position of a blood vessel wall is specified through comparison between an echo data level and a predetermined threshold, and the displacement of the blood vessel wall is tracked by detecting a change in the phase of an echo data signal. This is a known method.

Referring to echo data concerning the inside of a sample gate set on a measurement line (including a sample gate set in a Doppler beam direction (described later)), the velocity calculator 28 extracts Doppler information from the echo data to obtain information of speeds, and calculates a blood velocity as an averaged value of the speeds. A displacement signal 102 indicative of a blood vessel diameter, calculated in the displacement calculator 26, and a blood velocity signal 104 indicative of blood velocity, calculated in the velocity calculator 28, are supplied to the display processor 24 and the evaluation value calculator 34.

A measurement line setting section 30 is a means for use in setting a measurement line (described later), and a tracking gate setting section 32 is means for use in manually setting a tracking gate, both means comprising, for example, a pointing device such as a keyboard, a track ball, and so on.

Figure 2:
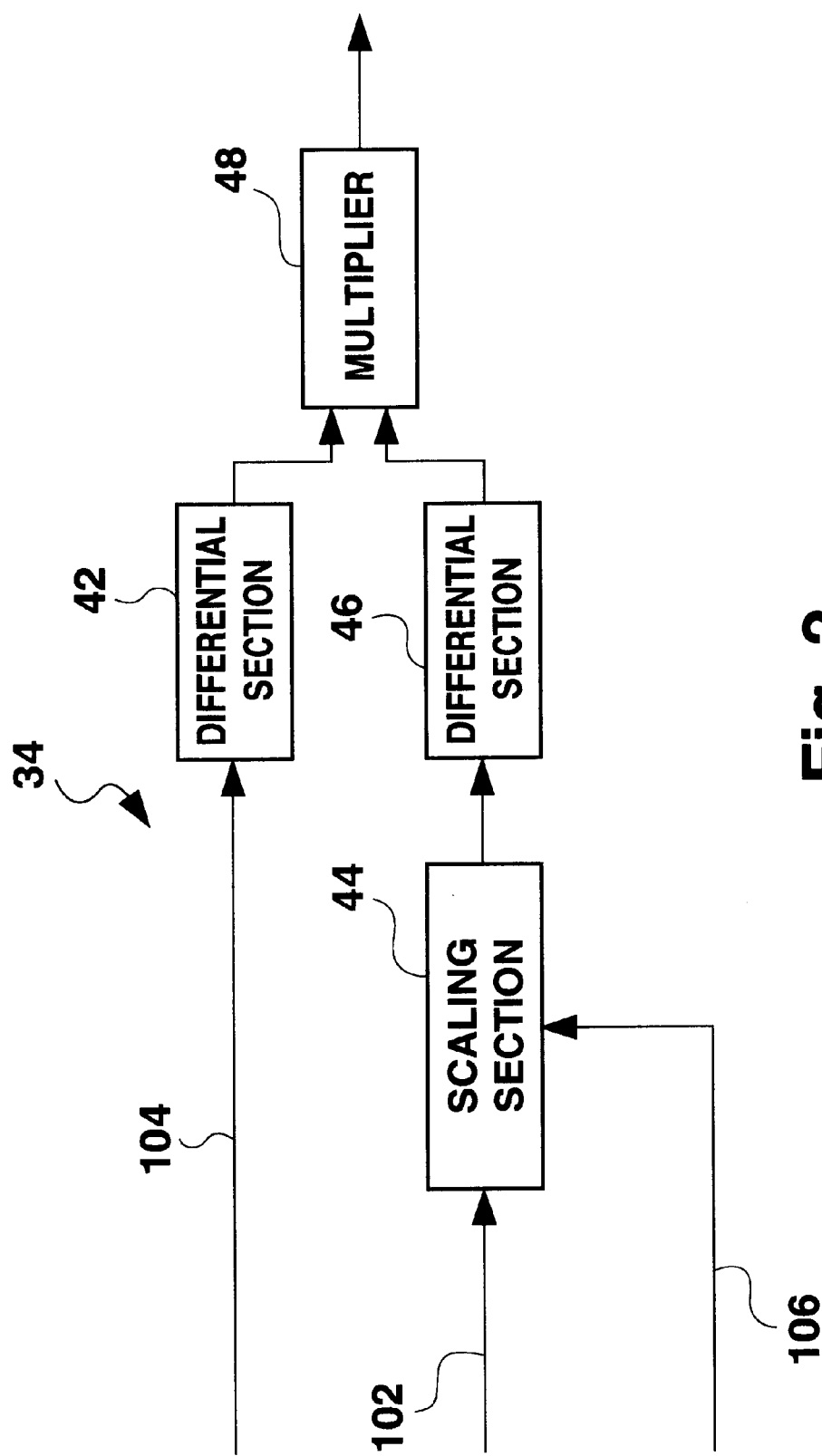
FIG. 2 is a diagram showing an example of a specific structure of an evaluation value calculator shown in FIG. 1.

The evaluation value calculator 34 calculates wave intensity as an evaluation value based on a blood vessel diameter and a blood velocity, as will be described later with reference to FIG. 2. The evaluation value calculator 34 may be made by means of either hardware or software. FIG. 2 (shown later) shows a specific structure of the evaluation value calculator 34. A value of wave intensity, calculated in the evaluation value calculator 34, is output to the display processor 24.

In this embodiment, data 106, specifically, data on the maximum and minimum blood pressure values, which is output from the hemodynamometer 38 for use in calculation of wave intensity in the evaluation value calculator 34, is referred to as a reference. Here, the hemodynamometer 38 may be of a cuff type to be worn around a subject's upper arm for blood pressure measurement, or a catheter type to be inserted into a subject's blood vessel, though the cuff-type hemodynamometer is preferable in consideration of the burden imposed on the subject.

A memory 40 is a storage device for storing data on the minimum and maximum blood pressure values registered or measured in the past for use in a case where a hemodynamometer 38 is not used. That is, when very accurate measurement is unnecessary, a waveform indicative of a change of a blood vessel diameter can be converted into a waveform indicative of a change in blood pressure based on the data stored in the memory 40.

The display processor 24 creates an image to be shown on a display 36. The display processor 24 has an image composition function, and so on. An exemplary display image for the display 36 will be described later with reference to FIGS. 3 and 4.

Note that, preferably, the velocity calculator 28 comprises a quadrature detector and an auto-correlator, which are installed in a conventional ultrasonic Doppler diagnostic apparatus. The display processor 24 is supplied with an electrocardiographic signal 107 from an electrocardiograph, so that the display 36 can present electrocardiogram.

FIG. 2 shows an example of a specific structure of a evaluation value calculator 34 of FIG. 1. A blood velocity signal 104 from the velocity calculator 28 is input to a differential section 42, which then calculates time differential of blood velocity to be output to the multiplier 48.

Meanwhile, a displacement signal 102 from the displacement calculator 26 and a blood pressure signal 106 from the hemodynamometer 38 are input to a scaling section 44, which then calibrates the waveform of a displacement signal 102 into a blood pressure waveform, using the maximum value of the displacement signal 102 as the maximum blood pressure value and the minimum value as the minimum blood pressure value. That is, the scaling section 44 carries out unit conversion to output a blood pressure waveform signal. Receiving the blood pressure waveform signal, the differential section 46 calculates a time differential of the received signal, and outputs a differential to a multiplier 48.

The multiplier 48 multiplies differentials of blood velocity and of blood pressure, respectively from the differential section 42 and the differential section 46, to obtain wave intensity as an evaluation value. That is, the structure of FIG. 2 constitutes a circuit for executing the equation (2). It should be noted that, when a sign inversion section is provided upstream of the differential section 42 so that a blood velocity signal 104 with an inverted sign is input to the structure of FIG. 2, the sign of the output signal from the differential section 42 may be inverted in order to adjust polarity (i.e., positive or negative), which is important for wave intensity, so as to agree with a calculation condition.

Figure 3:
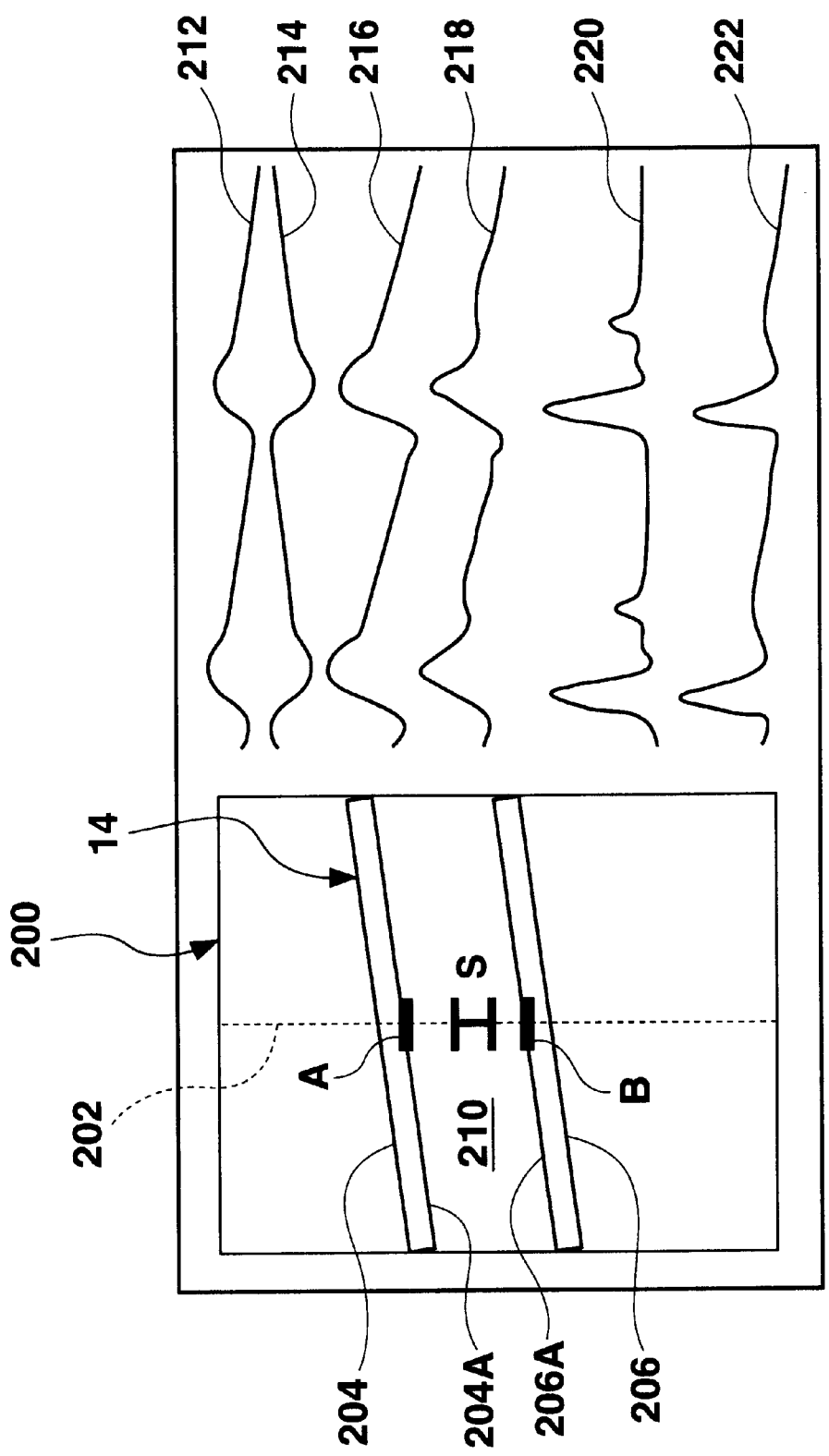
FIG. 3 is a diagram showing an example of a displayed image.

FIG. 3 shows an example of an image shown on the display 36 of FIG. 1. On the left half of the image is shown a tomogram 200. The tomogram 200 contains a longitudinal section image of a blood vessel 14. This means that the shown tomogram 200 is obtained with a probe properly positioned with respect to a blood vessel.

A measurement line 202 is set on the tomogram 200 by the user. In the example of FIG. 3, the measurement line 202 is set in one ultrasonic beam direction, which, however, is not a limited example. Alternatively, for example, when the direction of the measurement line 202 can be desirably set, measurement line 202 can be consistently set in a direction orthogonal to the center axis of the blood vessel 14.

Tracking gates A and B are set on the measurement line 202 by the user in this embodiment. Here, the tracking gate A is set including the intima 204A of the anterior wall 204, while the tracking gate B is set including the intima 206A of the posterior wall 206. Echo data in the tracking gates A and B is referred to in automatic specification of the intimae 204A, 206A using the level of the echo data as a reference. The positions of the intimae 204A and 206A are determined following displacement, if any, of the blood vessel 14. In this determination, specifically, a change of the phase of a received signal is referred to. This is a known method as described above.

In this example, when the positions of the blood vessel walls on both sides are specified, a sample gate S is automatically and dynamically set within the blood vessel 210, using the middle between the wall positions as a reference. The width of the sample gate S can be desirably set by the user.

Should the positions of the anterior wall 204 and posterior wall 206 be displaced due to pulsation, i.e., when the diameter of the blood vessel varies, the sample gate S is accordingly displaced. That is, this embodiment can offer an advantage such that a sample gate S can be accurately and dynamically set at the center in the blood vessel 14.

On the right half of the display screen are shown a plurality of graphs with their time axes aligned in parallel.

Specifically, there are shown a displacement waveform 212 concerning the anterior wall 204, specified by the tracking gate A, a displacement waveform 214 concerning the posterior wall 206, specified by the tracking gate B, and a change waveform 216 concerning the diameter of a blood vessel, calculated as a distance between the above mentioned two displacement waveforms. Below these waveforms are shown, from top to bottom in this order, a change waveform 218 concerning blood velocity, and another waveform 220 concerning wave intensity, calculated based on the change waveforms concerning the blood vessel diameter and the blood velocity. Electrocardiogram 222 is additionally shown as bio-information further below the above waveforms.

Therefore, according to exemplary display as shown in FIG. 3, the position of a sample gate S relative to a blood vessel can be clearly indicated by displaying the blood vessel 14 itself and a mark. This advantageously allows constant visual confirmation of the measurement point, which in turn results in improved measurement reliability. In addition, displaying of two or more graphs with their time axes aligned in parallel enables analysis on correlation between wave intensity and its underlying waveforms in evaluation of the wave intensity. Moreover, the simultaneous displaying of two or more graphs enables detection of a cause of any measurement error, which results in still further improvement of measurement reliability.

Figure 4:
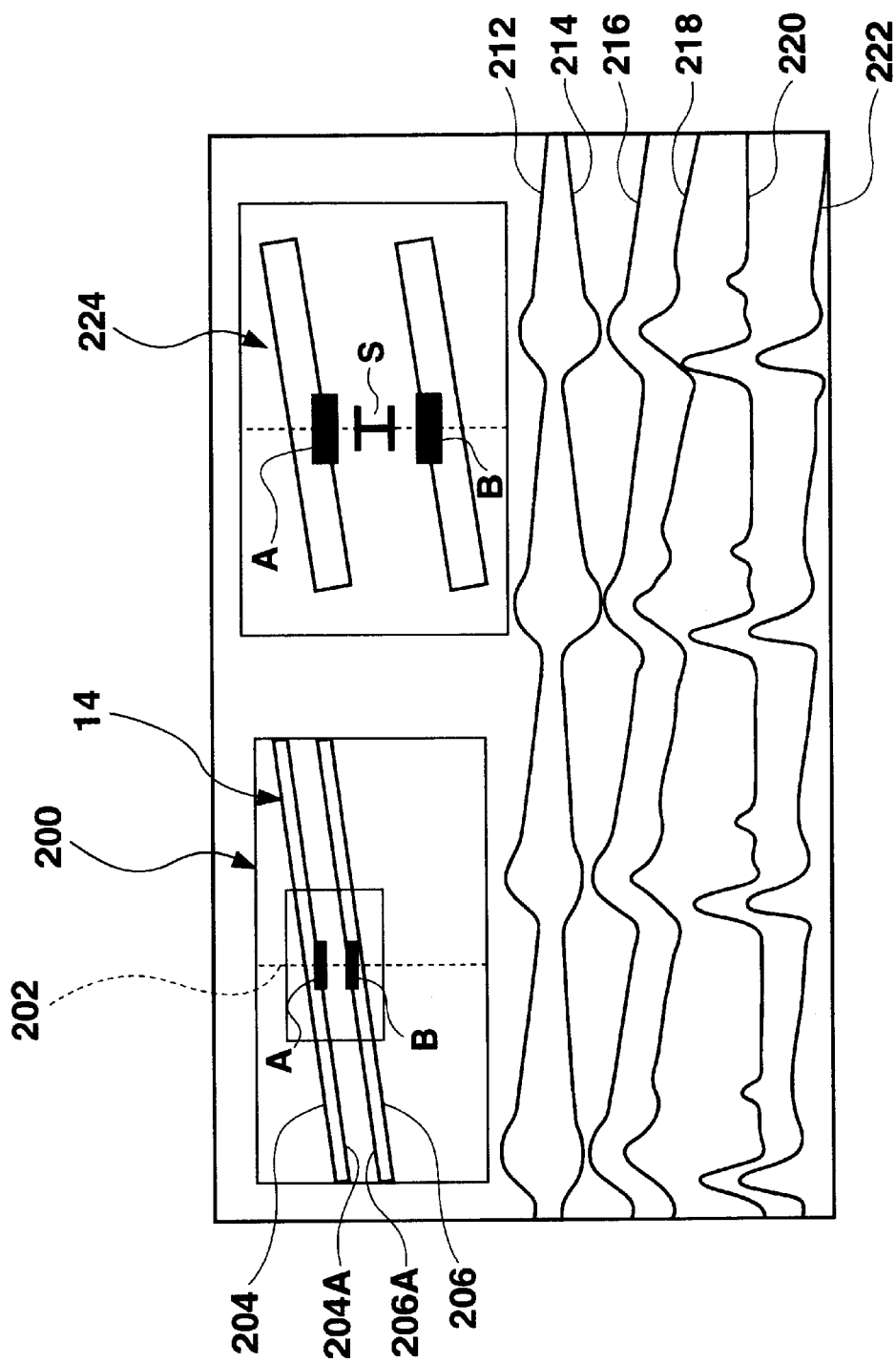
FIG. 4 is a diagram showing another example of a displayed image.

FIG. 4 shows another example of a displayed image, in which members identical to those in FIG. 3 are given identical reference numerals and description thereof is not repeated.

In the displayed example of FIG. 4, a tomogram 200 is shown on the upper left part in the display screen, and an enlarged image 224 of a focused part and its neighboring part in the tomogram 200 are shown in the upper right part. That is, display of an enlarged image 224 of, for example, a thin blood vessel enables more accurate setting of a tracking gate, as well as more accurate recognition of the position of a sample gate S.

In the lower part of the display screen, two ore more graphs are displayed with their time axes aligned in parallel, similar to the example in FIG. 3. Advantageously, displaying of a plurality of graphs enables comprehensive diagnosis of a blood vessel, the heart, and so on.

Figure 5A:
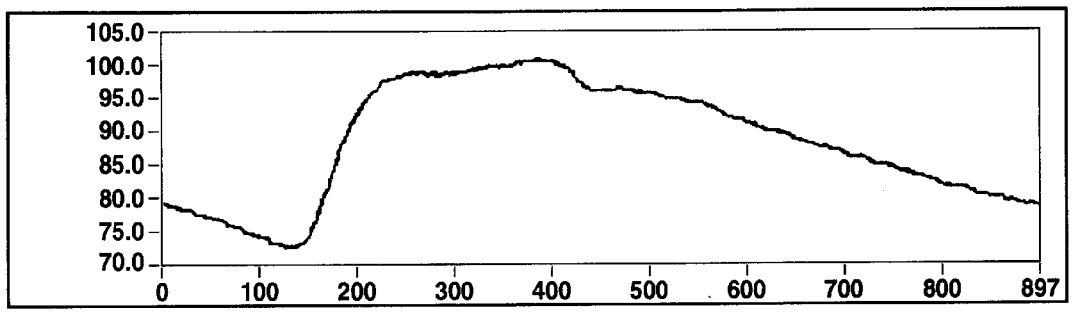
FIG. 5A is a diagram showing an example of actual measurement data concerning change of blood pressure.
Figure 5B:
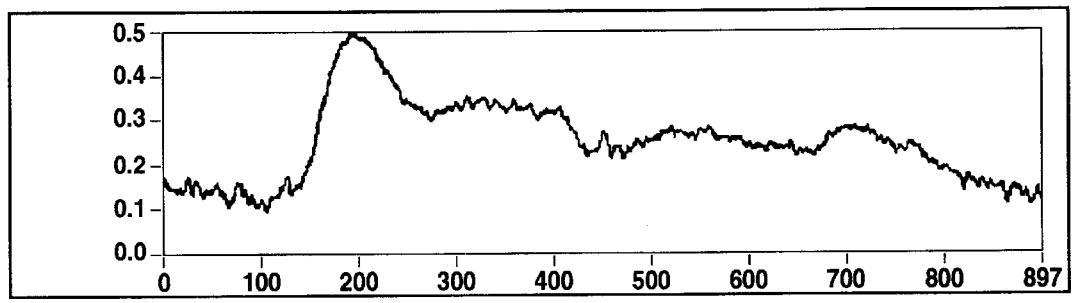
FIG. 5B is a diagram showing an example of actual measurement data concerning change of blood velocity.
Figure 5C:
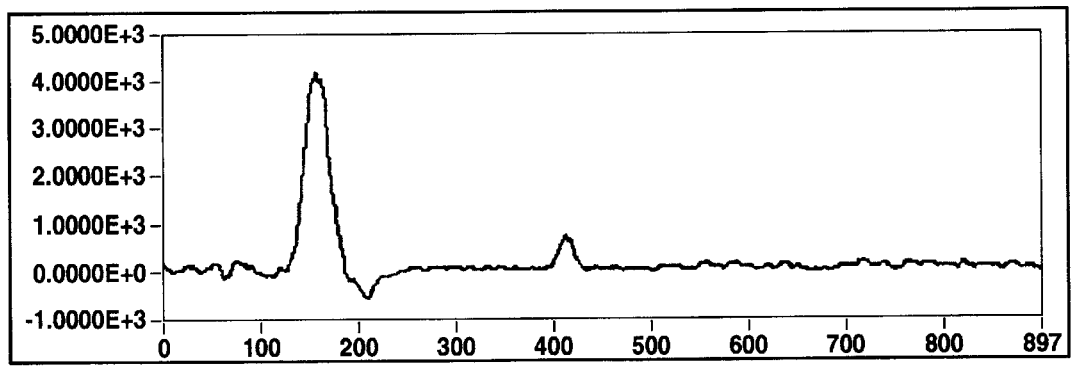
FIG. 5C is a diagram showing an example of actual measurement data concerning change of wave intensity over time.
Figure 5D:
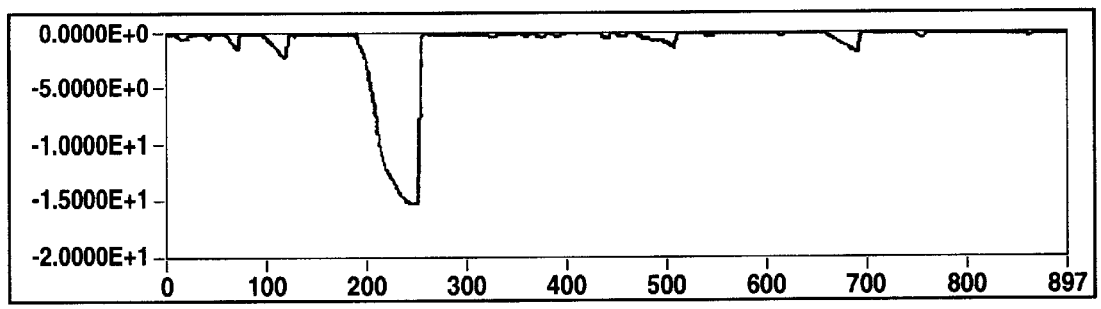
FIG. 5D is a diagram showing an example of actual measurement data concerning a negative area, or an area of a negative region of wave intensity.
Figure 5E:
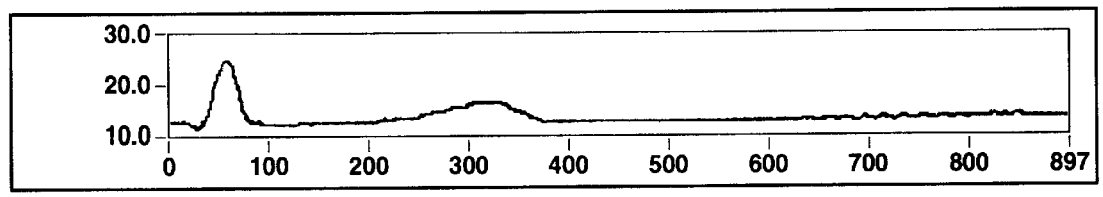
FIG. 5E is a diagram showing an example of actual measurement data concerning electrocardiogram.

FIGS. 5A, 5B, 5C, 5D and 5E present actual measurement data in a cardiac cycle; FIG. 5A shows a blood pressure change waveform; FIG. 5B shows a blood velocity change waveform; FIG. 5C shows a change waveform of wave intensity as time passes; FIG. 5D shows a negative area of wave intensity which indicates the effects of backward-traveling waves; and FIG. 5E shows an electrocardiogram. Needless to say that other values can be displayed as a bio-signal.

Figure 6:
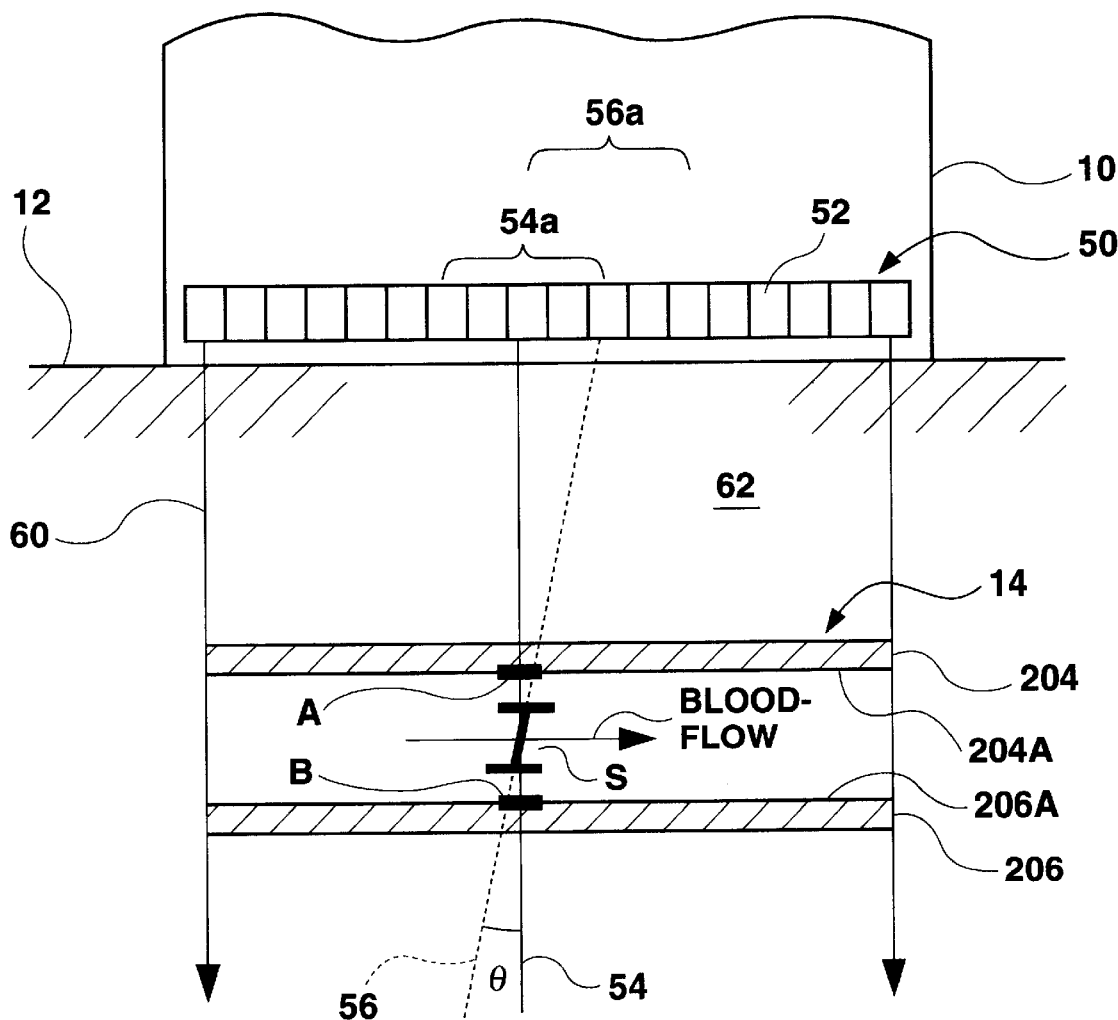
FIG. 6 is a diagram showing relationship between ultrasonic beams for displacement measurement and for Doppler measurement.

FIG. 6 is a diagram illustrating a beam setting method employable with the present embodiment. When a measurement line 54 is set just orthogonal to the center axis of the blood vessel 14, as shown, although this is convenient to calculate the diameter of a blood vessel, it is difficult, in view of its principle, to extract Doppler information from echo data obtained along that measurement line. Therefore, a beam direction for Doppler measurement is additionally set. Specifically, the transmission and reception control section 18 of FIG. 1 applies beam steering so that a Doppler beam direction, indicated by the reference numeral 56 in FIG. 6, is set. The Doppler beam direction 56 is set passing through the sample gate S and intersecting with the measurement line 54, or a beam direction for blood vessel diameter measurement, at an angle θ. In the above setting, the tracking gates A and B are set on the measurement line 54, while the sample gate S is set in the Doppler beam direction 56. The angle θ may be set at, for example, 15°.

A probe 10 has an array transducer 50, which comprises a plurality of transducer elements 52. In general, electronic scanning with ultrasonic beam 60 is achieved along the array direction of the array transducer 50 to form a scanning plane 62, so that a tomogram is formed.

After the tracking gates A,B is set, transmission and reception of ultrasonic beams are carried out on the measurement line and in the Doppler beam direction 56 in a predetermined time-sharing pattern. In this case, a transmission and reception port 54a is set so as to achieve ultrasonic transmission and reception in a direction corresponding to the measurement line 54, and a transmission and reception port 56a is set so as to achieve ultrasonic transmission and reception in a direction corresponding to the Doppler beam direction 56. For such control, the transmission and reception control section 18 receives position information concerning a measurement line set using the measurement line setting section 30 and information concerning the center of a blood vessel diameter. As described above, the transmission and reception control section 18 variably sets the position and direction of the Doppler beam direction 56 according to displacement, if occurs, of the blood vessel 14 and its center. This ensures constant setting of an appropriate sample gate S.

Figure 7:
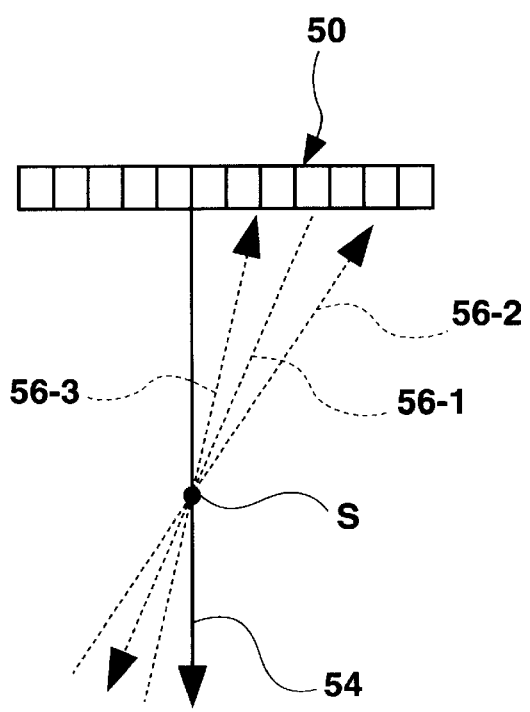
FIG. 7 is a diagram showing another example of beam setting.

FIG. 7 illustrates a modified example of a beam setting method. In this example, a beam for measuring displacement of a blood vessel wall is formed along the measurement line 54. In addition, a transmission beam 56-1 for Doppler measurement is set passing through the sample gate S, and two additional reception beams 56-2, 56-3 for Doppler measurement are also set intersecting with the transmission beam 56-1. With this arrangement, Doppler measurement is achievable even when the measurement line 54 is set orthogonal to a blood vessel axis. Moreover, a blood velocity vector can be obtained because so-called one transmission and two receptions are applied.

Figure 8:
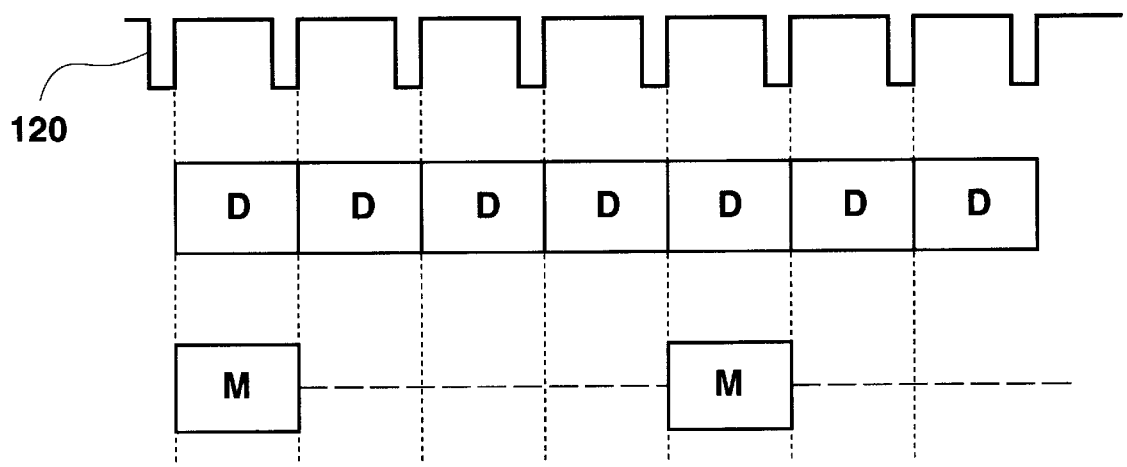
FIG. 8 is a diagram showing timing relationship between Doppler measurement and displacement measurement.

FIGS. 8 to 11 show timing charts for Doppler measurement and measurement of displacement of a blood vessel wall. In FIG. 8, the reference numeral 120 represents a pulse indicative of a repetitive cycle; the reference sign D represents a period for Doppler measurement, i.e., a velocity calculation; and the reference sign M represents a period for calculation of displacement of a blood vessel wall, i.e., blood vessel displacement measurement. In the example of FIG. 8, in which a pulse repetition frequency (PRF) is set, for example, at 4 kHz, Doppler measurement is continually and repetitively applied, whereas displacement measurement is conducted once for four Doppler measurements. That is, the chart of FIG. 8 concerns a case in which one beam direction is used for Doppler measurement and displacement measurement.

Figure 9:
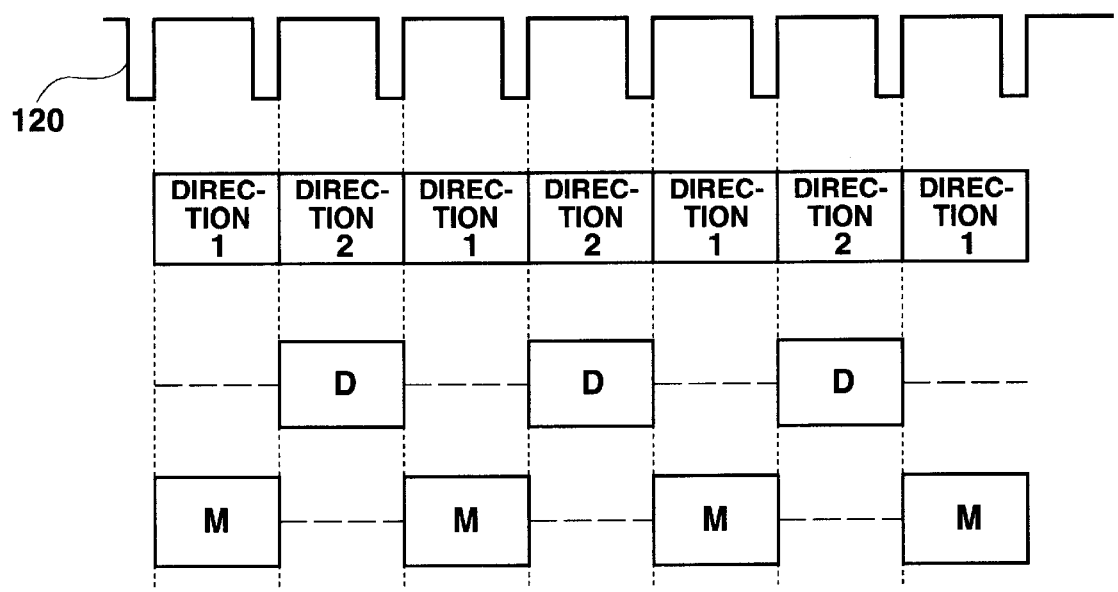
FIG. 9 is a diagram showing timing relationship between Doppler measurement and displacement measurement.
Figure 10:
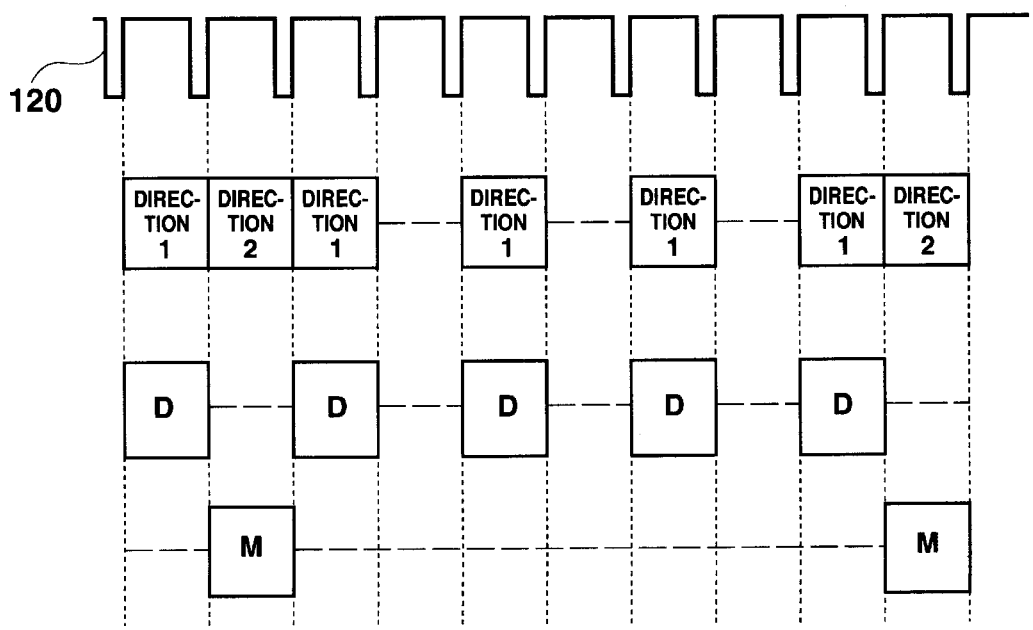
FIG. 10 is a diagram showing timing relationship between Doppler measurement and displacement measurement.
Figure 11:
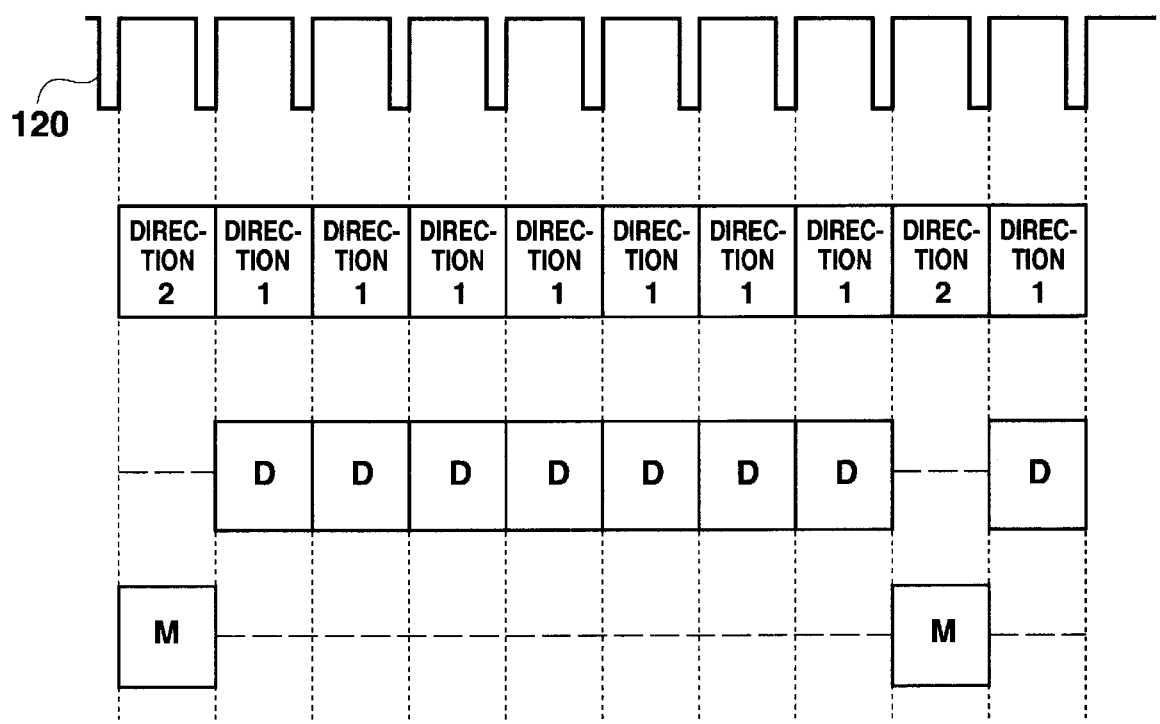
FIG. 11 is a diagram showing timing relationship between Doppler measurement and displacement measurement.

The charts of FIGS. 9 to 11, on the other hand, illustrate a case where two beam directions, i.e., a displacement measurement beam direction and a Doppler measurement beam direction, are set. In the example of FIG. 9, directions 1 and 2 are repetitively and alternately set, wherein displacement measurement is conducted in the direction 1 and Doppler measurement is conducted in the direction 2. In this case, an ultrasonic beam is transmitted alternatively in the directions 1 and 2. Therefore, supposing that the PRF is, for example, 2 kHz, substantial PRFs of Doppler measurement and displacement measurement are each 1 kHz.

In the example of FIG. 10, in which PRF is 8 kHz, a substantial PRF for Doppler measurement is 4 kHz, while that for displacement measurement is 1 kHz. In the example of FIG. 11, in which PRF is 8 kHz, a PRF for Doppler measurement is 8 kHz, while that for displacement measurement of 1 kHz. Note that these measurement patterns are only exemplary, and various other patterns are usable.

Figure 12:
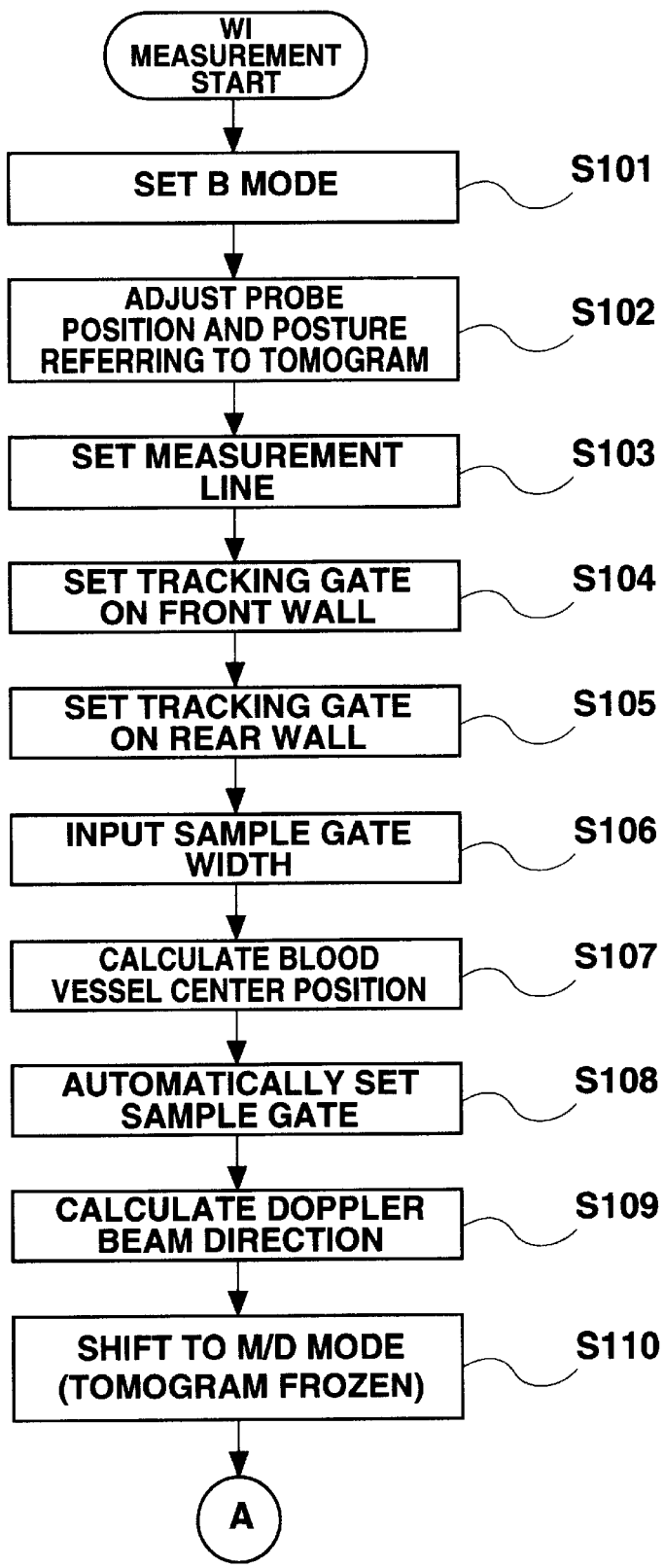
FIG. 12 is a flowchart for a measurement method according to the present invention.
Figure 13:
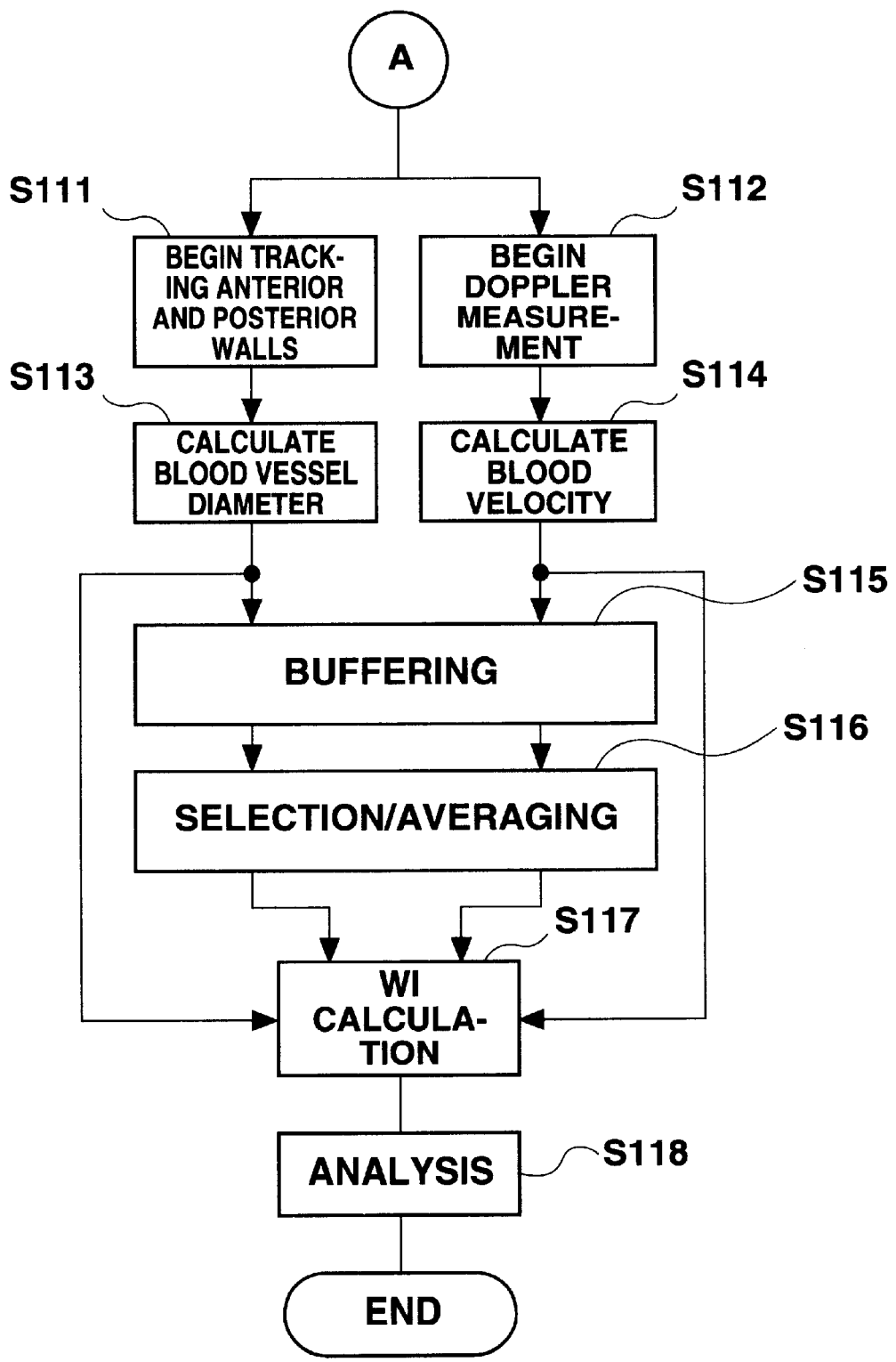
FIG. 13 is a flowchart for a measurement method according to the present invention.

FIGS. 12 and 13 show a flowchart of operation of the apparatus of FIG. 1.

At S101, a B mode measurement is set. That is, at S102, the position and posture of the probe 10 of FIG. 1 are desirably adjusted with respect to the B mode image, or a tomogram, such that a scanning plane is formed including the center axis of the blood vessel 14.

At S103, a measurement line 202, shown, for example, in FIG. 3, is manually set. At S104, a tracking gate A is manually set on the measurement line and the anterior wall. At S105, a tracking gate B is manually set on the posterior wall.

At S106, the width of a sample gate is set by a user. When this setting is not applied, a default value is set. At S107, the middle (a middle depth) between the positions (depth) of the tracked anterior and posterior walls is calculated.

At S108, a sample gate is automatically set so as to be of vertical symmetry using the middle as a reference. Specifically, the position of the sample gate is set following any displacement of a blood vessel wall.

At S109, a Doppler beam direction is calculated using the sample gate or the center of a blood vessel diameter as a reference. At S110, the B mode is switched to the M/D mode, in which the B mode image is generally frozen. In the M/D mode, a displacement measurement beam and a Doppler measurement beam, as shown in FIG. 6 are formed in a predetermined cycle.

Referring to FIG. 13, at S111, tracking of the anterior and posterior walls begins, while, at S112, Doppler measurement begins. At S113, a blood vessel diameter is calculated, and, at S114, a blood velocity is calculated as an averaged value of Doppler information.

In order to calculate wave intensity on a real time basis using the blood vessel diameter and the blood velocity respectively obtained at S113 and S114, S117 is conducted immediately after S113 and S114. At S117, a differential of a blood velocity and that of a converted value of a displacement signal are multiplied to thereby calculate wave intensity.

Meanwhile, for more accurate measurement less influenced by respiration, the blood vessel diameter and the blood velocity, respectively measured at S113 and S114, are first held in a buffer during a period corresponding to a predetermined number of heart pulses (S115). Then, data concerning stable and reproducible five pulses among the pulses held in the buffer are selected for averaging (S116).

At S117, wave intensity is calculated based on the averaged blood vessel diameter and blood velocity. At S118, a wave intensity waveform is analyzed upon necessity. Specifically, for example, first and second peaks may be specified, and a change of these waveforms may be analyzed.

As described above, the present invention as configured in this embodiment enables reliable setting of a measurement area with respect to a blood vessel, and simultaneous measurement of displacement of a blood vessel wall and a blood velocity, which resultantly improves measurement accuracy and reliability. In addition, simultaneously display of a plurality of items of related information on a display screen enables comprehensive evaluation of blood vessel condition and a heart function with reference to the displayed information.

Embodiment 2

In an ultrasonic diagnostic apparatus according to a second preferred embodiment of the present invention, a beam direction can be automatically set for measurement of displacement of a blood vessel wall or a blood velocity. Such an apparatus comprises a transmitter-receiver for transmitting and receiving an ultrasonic pulse for ultrasonic beam scanning to obtain a received signal; first beam direction setting means for determining a first beam direction orthogonal to a blood vessel wall, based on the received signal, to set the first beam direction to the transmitter-receiver; displacement measurement means for measuring displacement of a blood vessel wall using the received signal corresponding to the first beam direction; and evaluation value calculator for calculating an evaluation value using the displacement of the blood vessel wall.

Desirably, the first beam direction setting means includes beam steering means for steering a beam direction, characteristic signal detector for detecting a characteristic signal originated from the blood vessel wall with respect to the received signal in each of the respective beam directions resulting from the steering, and characteristic signal comparison means for mutually comparing characteristic signals concerning the respective beam directions to determine the first beam direction based on a result of comparison.

With such an arrangement, the beam steering means forms an ultrasonic beam in a plurality of beam directions. Generally, a distance between the transmitter-receiver and a blood vessel wall varies with the beam direction. Therefore, characteristic signals originated from respective parts of a blood vessel wall are each subjected to attenuation or delay by an extent commensurate with the distance over which the associated ultrasonic beam has traveled from transmission to reception which results in different characteristic signals. Therefore, a distance between the center of a transmission and reception port on a probe and a part of a blood vessel wall intersecting with each beam direction can be known through comparison of characteristic signals concerning the respective beam directions, and information concerning the arrangement and shape of a blood vessel can be obtained based on the distance information. The characteristic signal comparison means determines a first beam direction based on the information concerning the arrangement and shape of a blood vessel, obtained through comparison between characteristic signals concerning the respective beam directions.

An apparatus of the present invention may further comprise second beam direction setting means for setting a second beam direction for Doppler measurement, which inclines with respect to the first beam direction, to the transmitter-receiver, and blood velocity measurement means for measuring a blood velocity using the received signal corresponding to the second beam direction.

The blood velocity measurement means can measure a blood velocity using a Doppler measurement method. The blood velocity measurement means requires an ultrasonic beam intersecting with a blood vessel part where a blood velocity is to be measured, at an angle inclining with respect to the bloodstream. Using a first direction orthogonal to a blood vessel, i.e., a bloodstream, as a reference, the present apparatus determines a second beam direction inclining with respect to the first beam direction. Therefore, a resultant second beam direction inclines with respect to a bloodstream.

The present apparatus may further comprise an evaluation value calculator for calculating an evaluation value based on the displacement of a blood vessel wall and the blood velocity. The apparatus is employable with various evaluation values, with one example thereof being wave intensity.

The second beam direction setting means may set a sample gate in the first beam direction within the blood vessel based on, for example, a characteristic signal, and may further set a second beam direction passing through the sample gate.

The characteristic signal comparison means compares amplitudes of the characteristic signals concerning the respective received signals to determine the first beam direction. The amplitude of a characteristic signal depends on the angle formed by the associated ultrasonic beam direction and the blood vessel wall resulting in the characteristic signal. That is, basically, for an ultrasonic beam intersecting with a blood vessel wall at an angle closer to a right angle, the resultant characteristic signal has a larger amplitude. Therefore, the present apparatus can obtain information on the shape of a blood vessel wall with reference to the amplitude of an associated characteristic signal, and determine a first beam direction based on the shape information. Desirably, the characteristic signal comparison means determines the first beam direction using a characteristic signal as the maximum amplitude. At a point on a blood vessel wall resulting in a characteristic signal having the maximum amplitude, an ultrasonic beam intersects with the blood vessel wall at a right angle. In other words, a first beam direction orthogonal or nearly orthogonal to a blood vessel wall can be determined using a characteristic signal as the maximum amplitude.

Figure 14:
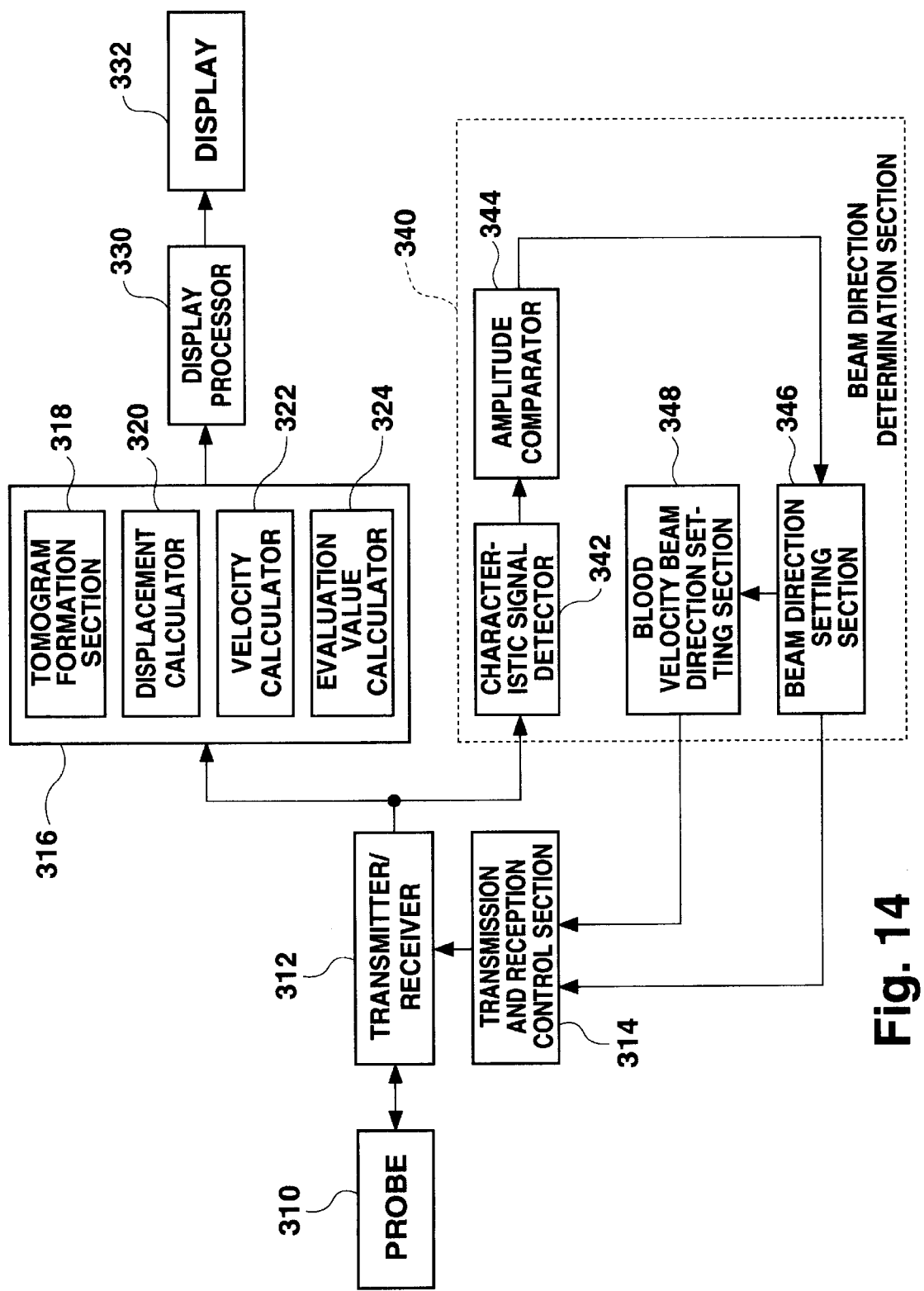
FIG. 14 is a block diagram showing a complete structure of a first ultrasonic diagnostic apparatus according to a second preferred embodiment of the present invention.

In the following, the present embodiment will be described using a more specific example. FIG. 14 is a block diagram showing a complete structure of a first type of an ultrasonic diagnostic apparatus capable of automatic setting of a beam direction in this example of the second preferred embodiment.

Referring to FIG. 14, a probe 310 is an ultrasonic probe for transmission of an ultrasonic pulse and reception of an echo. The probe 310 has an array transducer (described later) so that ultrasonic electronic scanning is carried out through control of driving timing of the array transducer. An electronic scanning method may include, for example, electronic linear scanning, electronic sector scanning, and the like.

A transmitter-receiver 312 comprises a transmission circuit for supplying a transmission signal to the probe 310 and a reception circuit for conducting amplification and phasing integration with respect to a signal received from the probe 310.

The transmission and reception control section 314 is responsible for transmission and reception control for formation of a transmission beam and a reception beam.

A received signal processor 316 comprises a tomogram formation section 318, a displacement calculator 320, a velocity calculator 322, and an evaluation value calculator 324. The tomogram formation section 318 forms a tomogram, or a B mode image, from a received signal. Image information concerning the formed tomogram is output to the display processor 330.

The displacement calculator 320 calculates displacement of the position of a blood vessel wall, and has a function for calculating a blood vessel diameter based on the positions of the anterior and posterior walls of the blood vessel. Specifically, the displacement calculator 320 has a function for tracking the position of a blood vessel wall on a measurement line (described later), using a tracking gate set by a user. As a blood vessel wall causes a relatively strong echo, comparison between an echo data level and a predetermined threshold enables detection of a strong characteristic signal originated from a blood vessel wall. Displacement of the blood vessel wall is tracked based on a characteristic signal. The displacement calculator 320 sets a sample gate on the displacement measurement line, so as to include the center of the blood vessel. The sample gate is used in setting a Doppler beam direction (described later).

In the Doppler beam direction, a blood velocity sample gate is set at a part close to an intersection with the displacement measurement line. Referring to the echo data concerning the inside of the blood velocity sample gate, the velocity calculator 322 extracts Doppler information from the echo data to obtain speed information, and calculates a blood velocity as an averaged value of the speeds.

A displacement signal indicative of a blood vessel diameter, calculated in the displacement calculator 320, and a blood velocity signal indicative of a blood velocity, calculated in the velocity calculator 322, are supplied to the display processor 330 and the evaluation value calculator 324.

The evaluation value calculator 324 calculates wave intensity as an evaluation value based on a blood vessel diameter and a blood velocity. Specifically, the evaluation value calculator 324 calculates a time differential of blood velocity based on a blood velocity signal and a time differential of blood pressure based on a displacement signal, and multiplies the resultant time differentials to each other. The result of multiplication is wave intensity.

The display processor 330 creates an image to be shown on a display 332. The display processor 330 has an image composition function, and so on.

The apparatus of the present example has an automatic beam direction setting function for automatically setting a displacement measurement line and a Doppler beam direction based on a received signal. This function is realized by the transmission and reception control section 314 and the beam direction determination section 340. With this function, a first beam direction and a second beam direction are set, the first beam direction being orthogonal to a blood vessel wall and serving as a displacement measurement line suitable for use in measurement of displacement of a blood vessel wall, the second beam direction serving as a Doppler beam direction inclining with respect to a bloodstream. Preferably, the automatic beam direction setting function is activated when the longitudinal section image of a blood vessel is shown in the tomogram, as the directions of the two beams are on the same scanning plane.

Upon user activation of the automatic beam direction setting function, the transmission and reception control section 314 controls the transmitter-receiver 312 so as to conduct ultrasonic transmission and reception in different beam directions. Namely, ultrasonic beams are transmitted from and received by the probe 310 at different angles.

The beam direction determination section 340 is supplied with received signals concerning the respective beam directions obtained through electronic scanning. The characteristic signal detector 342 checks the received signals concerning the respective beam directions, and detects strong echo originated from a blood vessel wall for use as a characteristic signal. It should be noted that, generally, a characteristic signal is obtained from each of the anterior and posterior walls of a blood vessel. The amplitude comparator 344 obtains the amplitude of one or both of the characteristic signals originated from the anterior and posterior signals for every beam direction. A larger amplitude is obtained for an ultrasonic intersecting with a blood vessel wall at an angle closer to a right angle. Therefore, the beam direction resulting in a signal having the maximum amplitude is expected to be orthogonal to a blood vessel wall. The amplitude comparator 344 of the present apparatus compares the amplitudes of the characteristic signals concerning the respective beam directions, and selects a beam direction resulting in a signal having the maximum amplitude as a first beam direction. When the amplitude is not maximized, the angle formed by a blood vessel wall and a beam direction resulting in a signal having the largest amplitude is assumed to be closest to a right angle within a scanning range, and that beam direction providing the largest amplitude is selected as the first beam direction.

The thus selected first beam direction is provided to the beam direction setting section 346, which, in turn, informs the transmission and reception control section 314 of the first beam direction.

The first beam direction is also supplied to the blood velocity beam direction setting section 348. The blood velocity beam direction setting section 348 then sets a direction inclining at a predetermined angle with respect to the first beam direction on the scanning plane, as a second beam direction (a Doppler beam direction), and informs the transmission and reception control section 314 of the second beam direction. Because the second beam direction is set so as to pass through the sample gate set by the displacement calculator 320 on the displacement measurement line, transmission and reception ports for ultrasonic beams in the first and second beam directions are basically displaced from each other. The above described blood velocity sample gate is set at a part near the center of a blood vessel in the Doppler beam direction, and the velocity calculator 322 measures the speed of a bloodstream flowing within the blood velocity sample gate.

For measurement of, for example, wave intensity, the transmission and reception control section 314 alternately sets a first beam direction and a second beam direction for use by the transmission and reception section 312, so that the received signal processor 316 alternately measures displacement of a blood vessel wall and blood velocity.

It should be noted that, in such a case, a blood vessel wall is straight and beam steering is applied.

Figure 15:
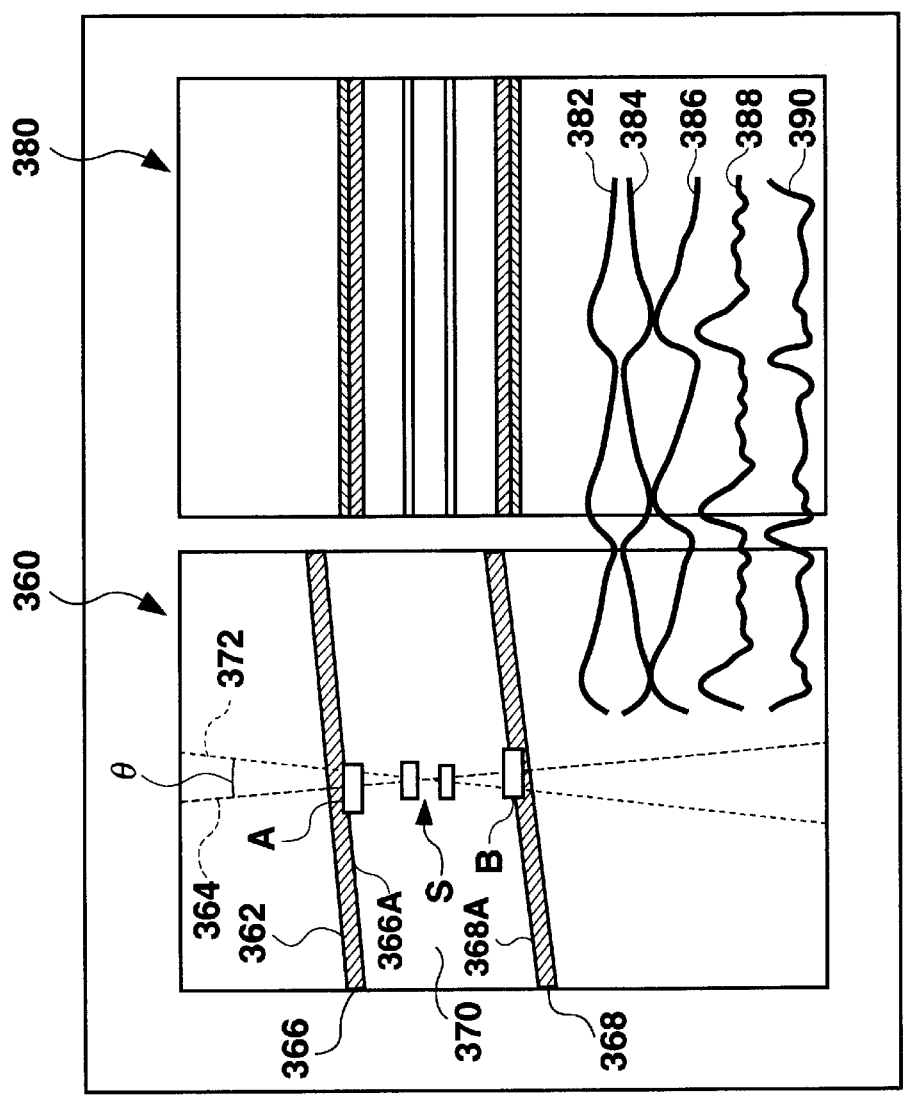
FIG. 15 is a diagram showing an example of a screen image shown on a display.

FIG. 15 shows an example of an image displayed on the display 332 of FIG. 14. On the left half of the image is shown a tomogram 360. The tomogram 360 contains a longitudinal section image of a blood vessel 362. This means that the shown tomogram 360 is obtained with a probe properly positioned with respect to a blood vessel.

In the tomogram 360, a first beam direction determined by means of the above described automatic beam direction setting function is set to serve as a displacement measurement line 364. Tracking gates A and B are set on the displacement measurement line 364 by the user such that the tracking gate A includes the intima 366A of the anterior wall 366 and the tracking gate B includes the intima 368A of the posterior wall 368. Echo data in the tracking gates A and B is referred to in automatic specification of the intimae 366A, 368A using the level of the echo data as a reference. Moreover, the positions of the intimae 366A and 368A are detected following the displacement, if occurs, of the blood vessel 62. This detection may be made, for example, based on a change of the phase of a received signal.

When the positions of the anterior and posterior walls are specified as above, the present apparatus automatically and dynamically sets a sample gate on the displacement measurement line within the blood vessel 370, using the middle between the wall positions as a reference. Further, a second beam direction is set as a Doppler beam direction by the blood velocity beam direction setting section 348, such that it passes through the set sample gate and incline at a predetermined angle θ with respect to the displacement measurement line 364. The resultant Doppler beam direction 372 is shown in the tomogram. A blood velocity sample gate S is set on the Doppler beam direction and also shown in the tomogram. The width of the sample gate S is freely settable by a user.

On the right half of the display screen are shown a plurality of graphs with time axes aligned in parallel. Specifically, there are shown an M mode image 380, a displacement waveform 382 concerning the anterior wall 366, tracked by the tracking gate A, a displacement waveform 384 concerning the posterior wall 368, tracked by the tracking gate B, and a change waveform 386 concerning the diameter of a blood vessel, calculated as a distance between the above mentioned displacement waveforms 382, 384. In the M mode image 380, echo on the displacement measurement line is shown in a time series manner. Below these waveforms are shown as bio-information, from top to the bottom in this order, a blood velocity waveform 388 concerning a bloodstream at the sample gate S, and an electrocardiogram 390, input from an electrocardiograph (not shown in FIG. 14). In addition, an evaluation value such as wave intensity, obtained from the evaluation value calculator 324, may be displayed.

Figure 16:
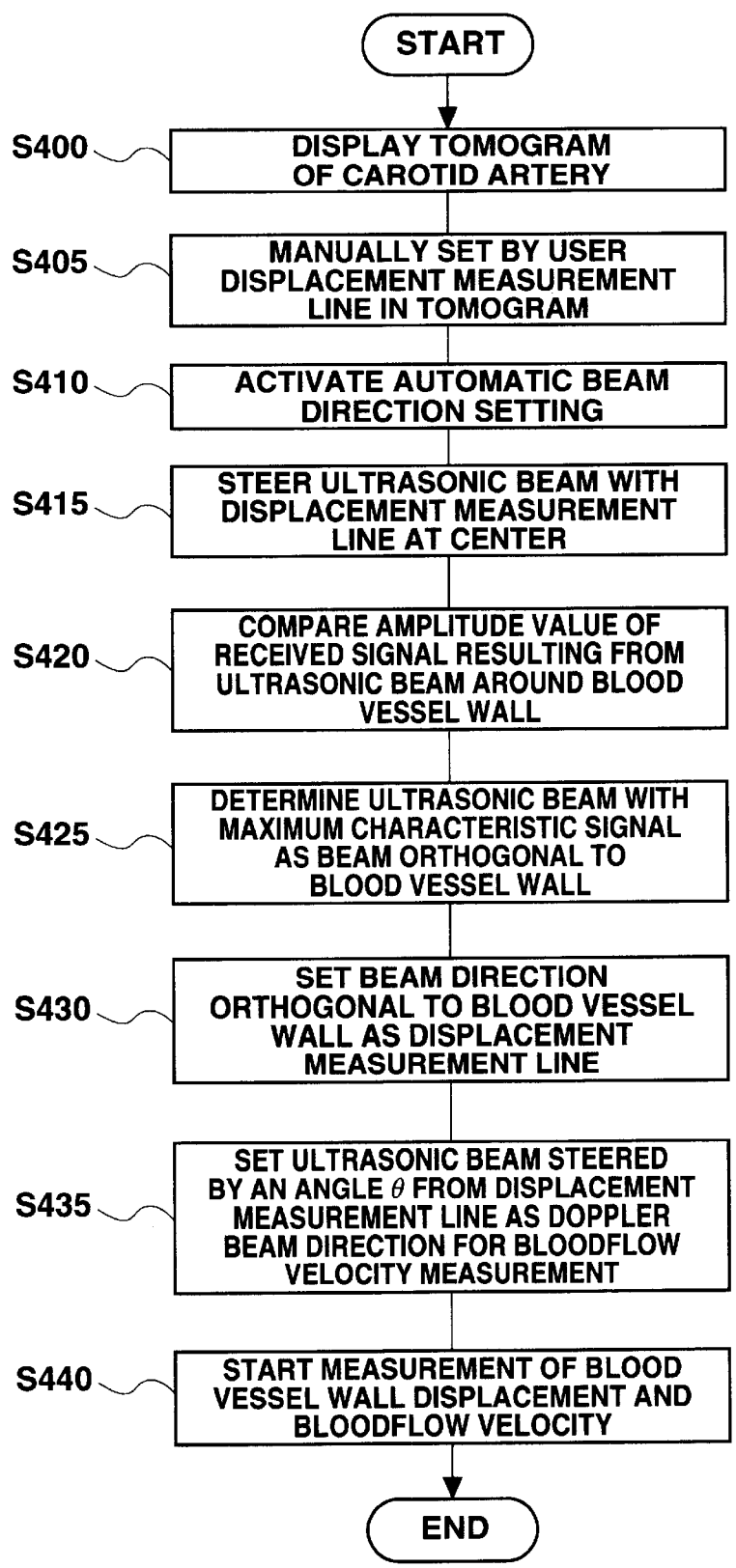
FIG. 16 is a flowchart explaining automatic beam direction setting operation.

FIG. 16 is a flowchart explaining operation of automatic beam direction setting applied by the present apparatus. A user operates the probe 310 so as to display a longitudinal section image of a part for diagnosis, for example, the carotid artery, on the display 332 (S400). The user then manually designates the displacement measurement line 364 shown in the tomogram as a target measurement position using a track ball and soon (S405). Although such a manually set displacement measurement line is sufficient for measurement of displacement of a blood vessel wall or the like, a more preferable displacement measurement line and Doppler line are set in the present embodiment, using the displacement measurement line as a reference. The automatic beam direction setting operation is activated by a user operating a button and so on provided to the present apparatus (S410).

The transmission and reception control section 314 conducts steering control with respect to an ultrasonic beam so that the beam sweeps back and forth centered around the displacement measurement line set by the user (S415). The amplitudes of the character signals concerning the respective beam directions resulting from the swinging ultrasonic beam are compared to one another in the amplitude comparator 344 (S420), so that a beam direction resulting in a characteristic signal having the maximum amplitude is determined as a first beam direction orthogonal to a blood vessel wall (S425). The first beam direction orthogonal to the blood vessel wall is set as a displacement measurement line obtained through automatic setting. This first beam direction is set by the beam direction setting section 346 and sent to the transmission and reception control section 314 at the time of measuring the displacement of a blood vessel wall (S430). Information on the set displacement measurement line is input to the blood velocity beam direction setting section 348. The blood velocity beam direction setting section 348 then sets a second beam direction as a Doppler beam direction for use in a blood velocity measurement, the second beam inclining at a predetermined angle θ with respect to the displacement measurement line and passing through the sample gate, which is set in a part close to the blood vessel center on the displacement measurement line (S435).

In the present example, a displacement measurement line and a Doppler beam direction are automatically set as described above, and the displacement of a blood vessel and blood velocity are measured using the set line and direction (S440).

It should be noted that, whereas a user designates a displacement measurement line before application of automatic beam direction setting, in order to designate the user's target measurement position in the above, user designation of a displacement measurement line is not necessary for automatic setting of the respective beam directions.

Figure 17:
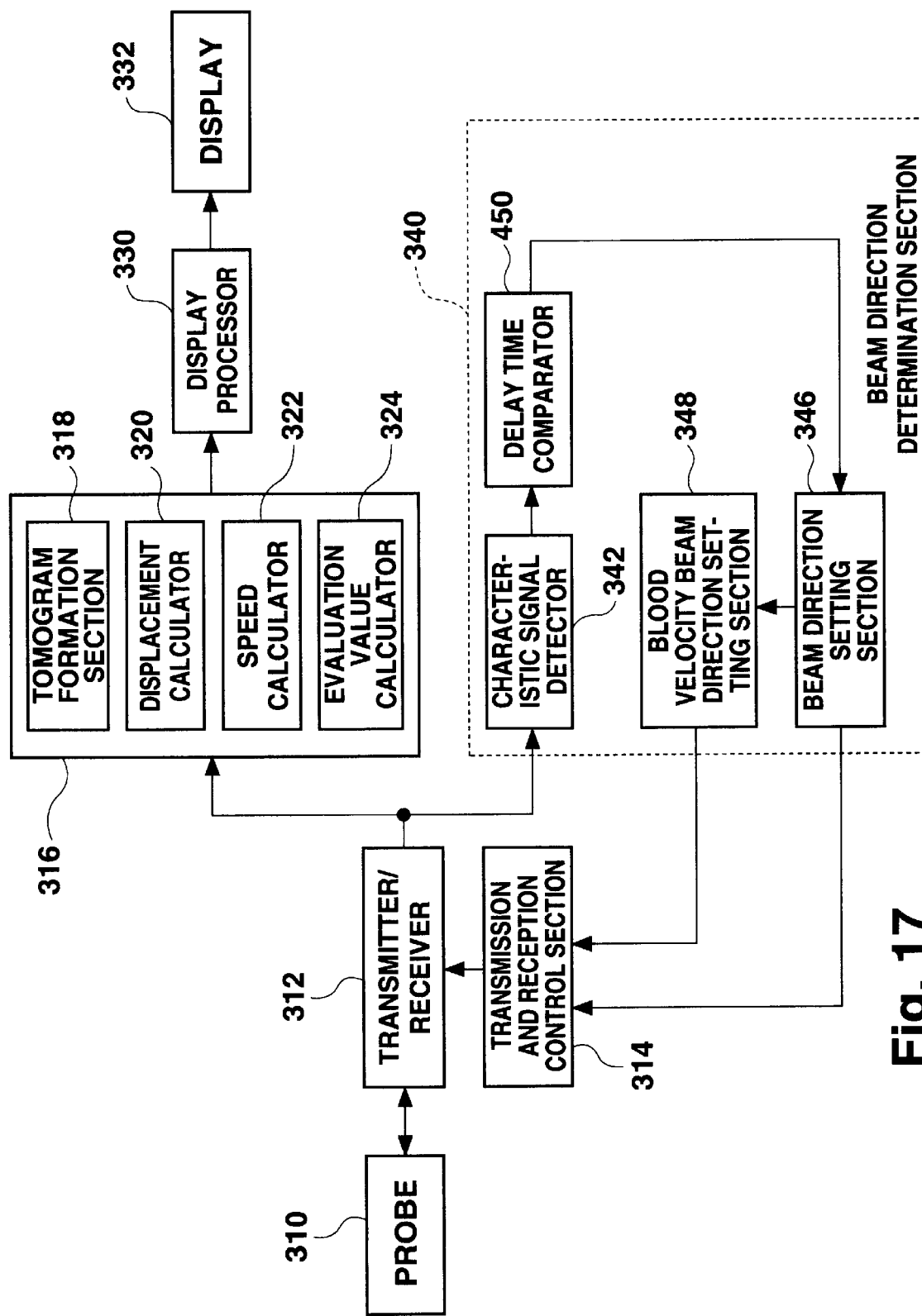
FIG. 17 is a diagram showing a complete structure of a second ultrasonic diagnostic apparatus according to a second preferred embodiment of the present invention.

FIG. 17 is a block diagram showing a complete structure of a second example of an ultrasonic diagnostic apparatus according to the second preferred embodiment, in which structural elements identical to those in FIG. 14 are given identical reference numbers and only briefly described.

The second example apparatus differs from the first example shown in FIG. 14 in that the former comprises a delay time comparator 450 in place of the amplitude comparator 344. That is, the second example apparatus determines a first beam direction using the delay time comparator 450. In the following, only the difference between the first and second examples are described and they are basically identical in all other points.

The characteristic signal detector 342 detects a characteristic signal originating from a blood vessel wall from among received signals concerning the respective beam directions resulting from beam steering by the transmission and reception control section 314. The delay time comparator 450 obtains a delay time from transmission of an ultrasonic beam to reception of a characteristic signal for every beam direction. A delay time becomes longer for a longer distance between a beam transmission port and a blood vessel wall reflecting the beam. Therefore, a beam direction resulting in the shortest delay time is expected to be orthogonal to the blood vessel wall. The delay time comparator 450 of the present apparatus compares the respective delay times, and selects a beam direction resulting in the minimum delay time as a first beam direction. In a case wherein delay time is minimized, the angle formed by a blood vessel wall and a beam direction resulting in the shortest delay time is assumed to be closest to a right angle within a scanning range, and that beam direction is selected as a first beam direction.

The thus selected first beam direction is supplied to the beam direction setting section 346, which, in turn, informs the transmission and reception control section 314 of this first beam direction.

Figure 18:
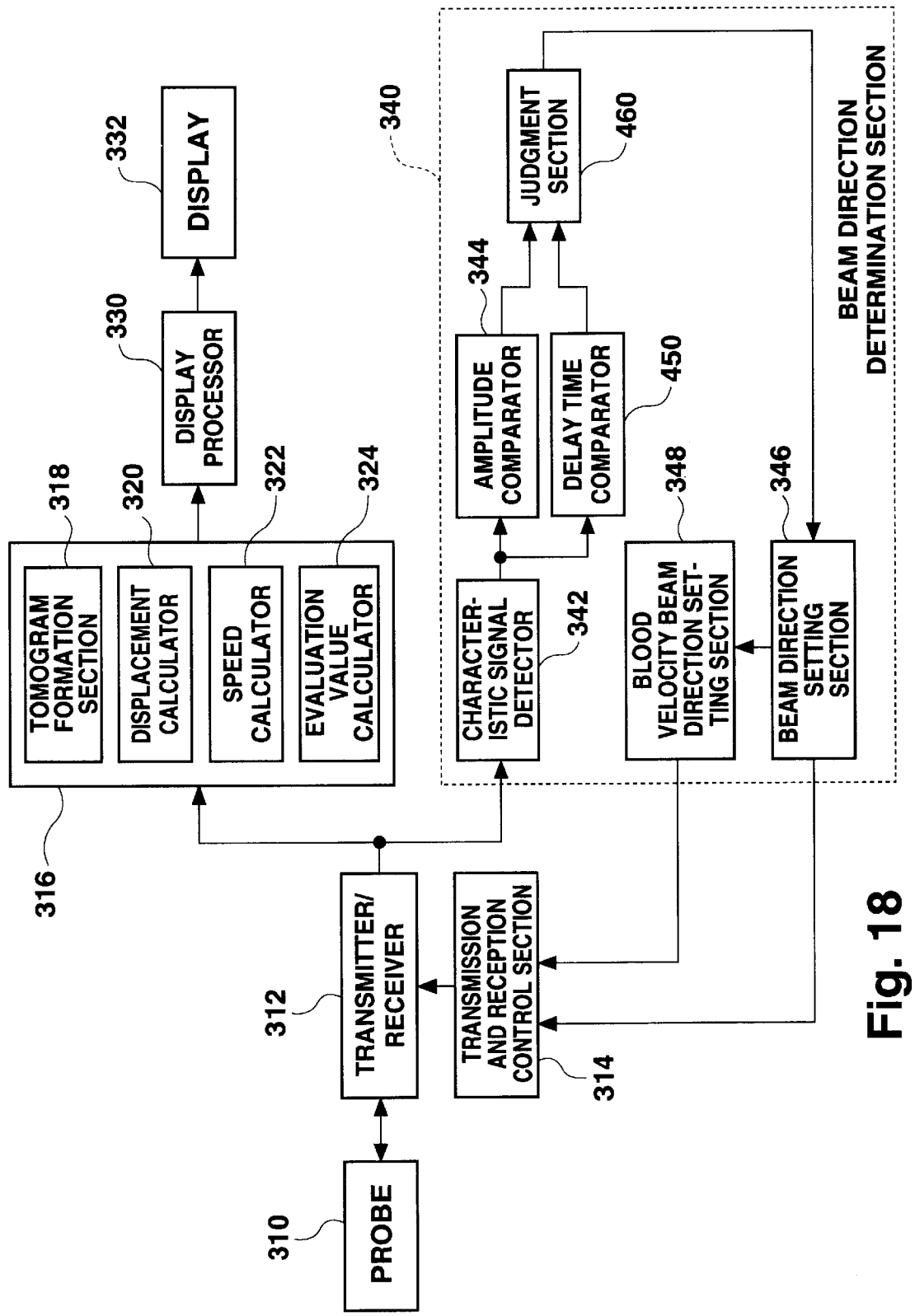
FIG. 18 is a diagram showing a complete structure of a third ultrasonic diagnostic apparatus according to the second preferred embodiment of the present invention.

FIG. 18 is a block diagram showing a complete structure of a third example ultrasonic diagnostic apparatus according to the second preferred embodiment, in which structural elements identical to those in FIG. 14 or 17 are given identical reference numbers and only briefly described.

The third example apparatus differs from the apparatuses of the first and second examples primarily in that the first beam direction is determined based on comparison results obtained in the amplitude comparator 344 and the delay time comparator 450. In the following, only the difference between the first and second types of apparatus and the third type of apparatus is described and they are basically identical as for other points.

A detection result concerning a characteristic signal, obtained in the characteristic signal detector 342, is supplied to the amplitude comparator 344 and the delay time comparator 450. The comparators 344 and 450 in turn supply their comparison results to a judgement section 460, which then determines a first beam direction based on the supplied comparison results.

In an example wherein the amplitude comparator 344 is configured so as to select a beam direction resulting in a signal having the maximum amplitude and the delay time comparator 450 is configured so as to select a beam direction resulting in a signal having the minimum delay time, the judgement section 460 can determine a direction at the middle of these directions as a first beam direction.

A delay time is proportional to a distance between the center of a transmission and reception port and a blood vessel wall reflecting the ultrasonic beam, while a signal amplitude exponentially attenuates as an increase of the distance. Therefore, a delay time and a logarithm of a signal amplitude are appropriately weighed and averaged, and a direction resulting in an averaged value being an extreme may be determined as a first beam direction.

As described above, according to the present invention, a blood vessel diameter, blood velocity, and so on can be measured with high accuracy, and an evaluation value can be calculated based thereon. This enables highly reliable ultrasonic diagnosis.

What is claimed is:

1. An ultrasonic diagnostic apparatus, comprising:
   a single transmitter-receiver for transmitting an ultrasonic pulse and obtaining echo data;
   a tomogram generator for forming a tomogram of a blood vessel based on the echo data;
   a measurement line setting device for setting a measurement line in the tomogram;
   a displacement calculator for calculating displacement of a blood vessel wall on the measurement line;
   a sample gate generator for automatically setting a sample gate using the measurement line as a reference;
   a blood velocity calculator for calculating blood velocity at the sample gate; and
   a wave intensity calculator for calculating a wave intensity based on the displacement of the blood vessel wall and the blood velocity.

2. An apparatus according to claim 1, wherein
   a displacement waveform corresponding to displacement of the blood vessel wall over time, and a velocity waveform indicative of change over time of the blood velocity are displayed together with the tomogram.

3. An apparatus according to claim 2, wherein
   a wave intensity waveform indicative of change over time of the wave intensity is additionally displayed.

4. An apparatus according to claim 3, wherein
   a bio-signal waveform is additionally displayed.

5. An apparatus according to claim 4, wherein
   the displacement waveform, the velocity waveform, the wave intensity waveform, and the bio-signal waveform are displayed on a real time basis with their time axes aligned in parallel.

6. An apparatus according to claim 1, wherein
   the measurement line setting device is an input device through which the user can designate the measurement line.

7. An apparatus according to claim 1, further comprising
   a tracking circuit for tracking a position of the blood vessel wall on the measurement line, following any motion of the blood vessel wall,
   wherein
   the displacement of the blood vessel wall is calculated from a result of tracking of the position of the blood vessel wall.

8. An apparatus according to claim 7, wherein
   the sample gate generator dynamically sets the sample gate within the blood vessel so as to follow the position of the blood vessel wall tracked.

9. An apparatus according to claim 1, wherein
a direction of the measurement line is determined as a first beam direction for displacement measurement, and
a direction passing through the sample gate and intersecting with the measurement line is determined as a second beam direction for Doppler measurement.

10. An apparatus according to claim 9, wherein
the transmitter-receiver includes an array transducer comprising a plurality of ultrasonic transducer elements, and
the array transducer carries out transmission and reception of an ultrasonic beam in the first direction and transmission and reception of an ultrasonic beam in the second direction in a time sharing manner.

11. An ultrasonic diagnostic apparatus, comprising:
a single transmitter-receiver for transmitting an ultrasonic pulse and obtaining echo data;
a tomogram generator for forming a tomogram of a blood vessel based on the echo data;
a measurement line setting device for setting a measurement line in the tomogram;
a blood vessel diameter calculator for calculating a blood vessel diameter along the measurement line;
a sample gate generator for automatically setting a sample gate using the measurement line as a reference;
a blood velocity calculator for calculating blood velocity at the sample gate;
a blood pressure calculator for converting a change of the blood vessel diameter into a change of blood pressure using a maximum blood pressure value input and a minimum blood pressure value input, as a reference; and
a wave intensity calculator for calculating a wave intensity based on the blood pressure and the blood velocity.

12. An apparatus according to claim 11, wherein
the blood pressure calculator considers the largest blood vessel diameter to be the maximum blood pressure value and the smallest blood vessel diameter to be the minimum blood pressure value during conversion into blood pressure.

13. An apparatus according to claim 11, wherein
the maximum blood pressure value and the minimum blood pressure value are measured using a hemodynamometer applied to a specific part of a subject.

14. An apparatus according to claim 11, wherein
the wave intensity calculator calculates a time differential of the blood pressure and a time differential of the blood velocity; and the wave intensity calculator further calculates wave intensity based on a product obtained by multiplying the time differential of the blood pressure and the time differential of the blood velocity.

15. An ultrasonic diagnostic apparatus, comprising:
a single transmitter-receiver for transmitting an ultrasonic pulse and obtaining echo data;
a calculator for calculating blood velocity at a measurement part within a blood vessel based on the echo data;
a calculator for calculating a time differential of the blood velocity;
a calculator for calculating blood pressure at the measurement part based on one or both of the echo data and a bio-measurement signal;
a calculator for calculating a time differential of the blood pressure; and
a calculator for multiplying the time differential of the blood velocity and the time differential of the blood pressure at a same moment to thereby calculate wave intensity.

16. An apparatus according to claim 15, further comprising:
a display device for forming a tomogram of the blood vessel based on the echo data, and displaying on a display screen the tomogram together with a waveform indicative of change over time of the blood velocity and another waveform indicative of change over time of the blood pressure; and
a mark indicator for displaying a mark indicative of the measurement part in the tomogram of the blood vessel displayed on the display screen.

17. An apparatus according to claim 16, wherein
the display device displays on a real time basis a waveform indicative of change of the wave intensity over time, together with the tomogram of the blood vessel.

18. An ultrasonic diagnostic apparatus, comprising:
a single transmitter-receiver for setting a beam direction passing across a blood vessel, transmitting an ultrasonic pulse in the beam direction, and obtaining echo data in the beam direction;
a blood velocity calculator for calculating blood velocity based on the echo data;
a blood vessel wall specifying circuit for specifying positions of an anterior wall and a posterior wall of the blood vessel based on the echo data obtained in the beam direction;
a blood vessel diameter calculator for calculating a blood vessel diameter based on the positions of the anterior wall and the posterior wall of the blood vessel;
a blood pressure calculator for converting a change over time of the blood vessel diameter to a change over time of a blood pressure value; and
a wave intensity calculator for calculating a wave intensity from a change over time of the blood velocity and the change over time of the blood pressure value.

19. An apparatus according to claim 18, wherein
the change over time of the blood vessel diameter is converted into a change over time of the blood pressure according to reference data.

20. An apparatus according to claim 19, wherein
the reference data is obtained using a hemodynamometer externally applied to a specific part of a subject.

21. An ultrasonic diagnostic apparatus, comprising:
a blood velocity calculator for preparing a blood velocity graph showing change over time of velocity of blood flowing in a blood vessel based on echo data;
a blood vessel diameter calculator for preparing a blood vessel diameter graph showing a change as time passes of a blood vessel diameter based on the echo data;
a wave intensity calculator for calculating a wave intensity from the blood velocity and the blood vessel diameter at a same moment and preparing a wave intensity graph showing a change as time passes of the wave intensity; and
a display device for simultaneously displaying the blood velocity graph, the blood vessel diameter graph, and the wave intensity graph.

22. An ultrasonic diagnostic apparatus, comprising:
a tomogram generator for forming a tomogram of a blood vessel based on echo data;

a blood velocity calculator for preparing a blood velocity graph showing change over time of the velocity of blood flowing in the blood vessel based on the echo data;

a blood vessel diameter calculator for preparing a blood vessel diameter graph showing change over time of a blood vessel diameter based on the echo data;

a wave intensity calculator for preparing a wave intensity graph showing change over time of the wave intensity based on the velocity of blood flowing in the blood vessel and the blood vessel diameter; and a display device for simultaneously displaying the tomogram of the blood vessel, the blood velocity graph, the blood vessel diameter graph.

23. An ultrasonic diagnostic apparatus, comprising:

a single transmitter-receiver for transmitting and receiving a ultrasonic pulse for ultrasonic beam scanning to obtain a received signal;

a first beam direction setting circuit for determining a first beam direction orthogonal to a blood vessel wall, based on the received signal, to set the first beam direction to the transmitter-receiver;

a displacement measurement circuit for measuring displacement of a blood vessel wall using the received signal corresponding to the first beam direction; and a wave intensity calculator for calculating a wave intensity using the displacement of the blood vessel wall.

24. An apparatus according to claim 23, wherein the predetermined angle is a right angle.

25. An apparatus according to claim 23, wherein the first beam direction setting circuit, including a beam steering circuit for steering a beam direction, a characteristic signal detector for detecting a characteristic signal originated from the blood vessel wall from among received signals relative to each of the respective beam directions resulting from the steering; and a characteristic signal comparison circuit for mutually comparing characteristic signals concerning the respective beam directions to determine the first beam direction based on a result of comparison.

26. An apparatus according to claim 25, wherein the characteristic signal comparison circuit mutually compares amplitudes of the characteristic signals among the respective received signals to determine the first beam direction.

27. An apparatus according to claim 26, wherein the characteristic signal comparison circuit determines the first beam direction utilizing a fact that a characteristic signal has the maximum amplitude.

28. An apparatus according to claim 25, wherein the characteristic signal comparison circuit determines the first beam direction through comparison of generation timing of the characteristic signals among the respective received signals.

29. An apparatus according to claim 28, wherein the characteristic signal comparison circuit determines the first beam direction using a time period from transmission of the ultrasonic beam to reception of the character signal as the minimum.

30. An apparatus according to claim 25, wherein the characteristic signal comparison circuit determines the first beam direction through comparison of generation timing and an amplitude of the characteristic signals among the respective received signals.

31. An apparatus according to claim 23, further comprising:

a second beam direction setting circuit for setting a second beam direction for Doppler measurement to the transmitter-receiver, the second beam direction inclining with respect to the first beam direction; and a blood velocity measurement circuit for measuring blood velocity using the received signal corresponding to the second beam direction.

32. An apparatus according to claim 31, wherein the wave intensity calculator calculates the wave intensity from the displacement of the blood vessel wall and the blood velocity.

33. An apparatus according to claim 31, wherein the second beam direction setting circuit sets a sample gate in the first beam direction within the blood vessel based on the characteristic signal, and further sets the second beam direction passing through the sample gate.

* * * * *